United States Patent
Gotthardt et al.

(10) Patent No.: US 9,040,238 B2
(45) Date of Patent: May 26, 2015

(54) POLYNUCLEOTIDES FOR USE IN MEDICINE

(75) Inventors: Michael Gotthardt, Berlin (DE);
Norbert Hübner, Berlin (DE); Marion Lewis Greaser, Middleton, WI (US);
Wei Guo, Madison, WI (US)

(73) Assignee: MAX-DELBRÜCK-CENTRUM FÜR MOLEKULARE MEDIZIN BERLIN-BUCH, Berlin (DE)

( * ) Notice: Subject to any disclaimer, the term of this patent is extended or adjusted under 35 U.S.C. 154(b) by 267 days.

(21) Appl. No.: 13/380,147

(22) PCT Filed: Jun. 22, 2010

(86) PCT No.: PCT/EP2010/003743
§ 371 (c)(1),
(2), (4) Date: Jul. 18, 2012

(87) PCT Pub. No.: WO2010/149332
PCT Pub. Date: Dec. 29, 2010

(65) Prior Publication Data
US 2012/0277282 A1    Nov. 1, 2012

Related U.S. Application Data

(60) Provisional application No. 61/219,125, filed on Jun. 22, 2009.

(51) Int. Cl.
*C07H 21/00* (2006.01)
*C07H 21/02* (2006.01)
*C12Q 1/68* (2006.01)

(52) U.S. Cl.
CPC ............ *C12Q 1/6853* (2013.01); *C12Q 1/6883* (2013.01); *C12Q 2535/125* (2013.01); *C12Q 2535/131* (2013.01)

(58) Field of Classification Search
USPC ................ 435/6.11, 6.12, 91.1; 530/350; 536/23.1, 24.3, 24.31
See application file for complete search history.

(56) References Cited

PUBLICATIONS

P.T. Ellinor et al., "A Novel Locus for Dilated Cardiomyopathy, Diffuse Myocardial Fibrosis, and Sudden Death on Chromosome 10q25-26," Journal of the American College of Cardiology, 2006, pp. 106-111, vol. 48, No. 1.
K.M. Brauch et al., "Mutations in RNA Binding Protein Gene Cause Familial Dilated Cardiomyopathy," Journal of the American College of Cardiology, 2009, pp. 1-16, vol. 54, No. 10.
D.L. et al., "Identification of Novel Mutations in RBM20 in Patients with Dilated Cardiomyophy," Clinical and Translational Science (CTS), 2010, XP-002625766, pp. 90-97, vol. 3, Issue 3.
International Search Report for PCT/EP2010/003743 dated Mar. 14, 2011.
Written Opinion of the International Searching Authority for PCT/EP2010/003743 dated Mar. 14, 2011.
Communication Pursuant to Article 94(3) EPC for European Patent Application No. 10736605.6 dated Sep. 30, 2013.

*Primary Examiner* — Jane Zara
(74) *Attorney, Agent, or Firm* — Ryan, Mason & Lewis, LLP

(57) ABSTRACT

The invention refers to polynucleotides selected from the group consisting of a) polynucleotides encoding for the polypeptide RBM20 comprising a P638L mutation for a human polypeptide RBM20, or a P641L mutation for a rat polypeptide RBM20, b) polynucleotides with a reverse complementary sequence of the polynucleotide of a) above, and c) polynucleotides with an identity at least 50% to a polynucleotide of a) or b) above.

9 Claims, 24 Drawing Sheets

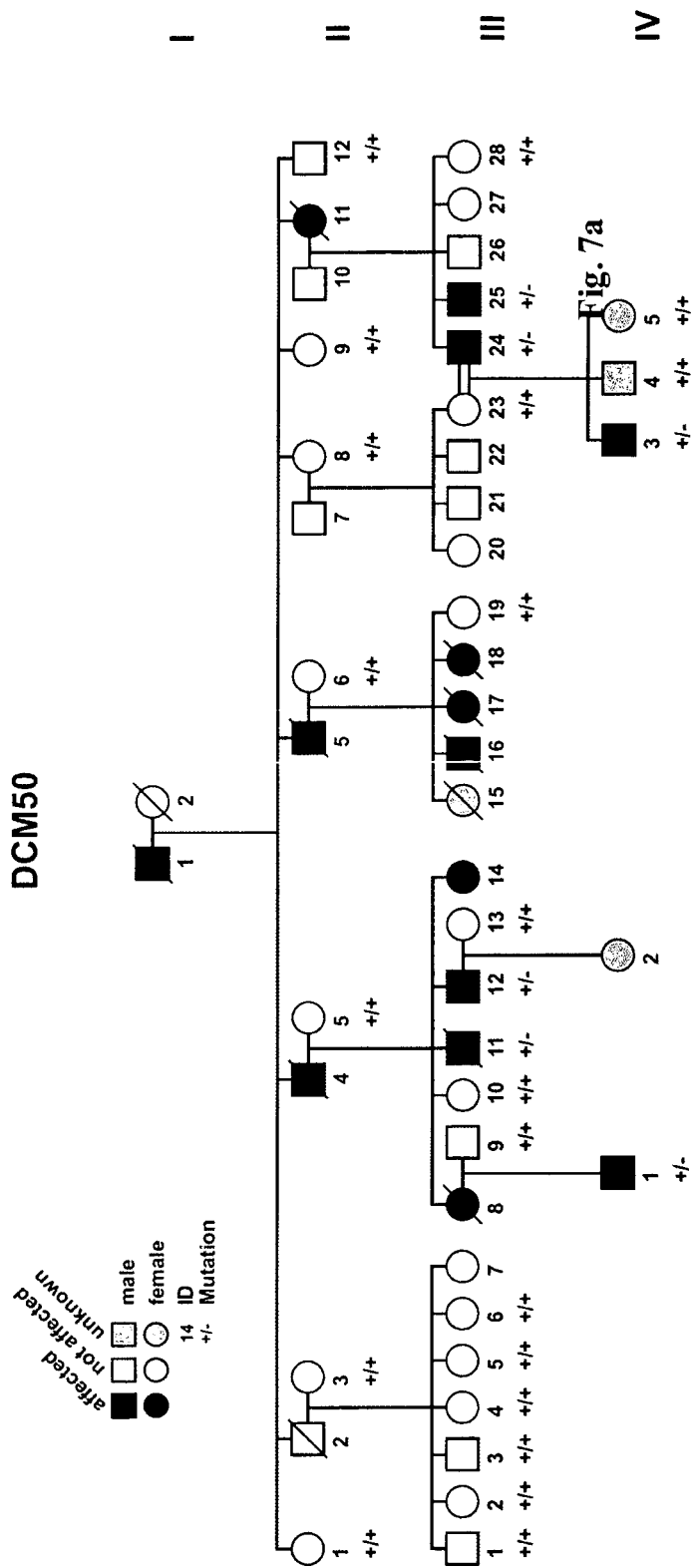

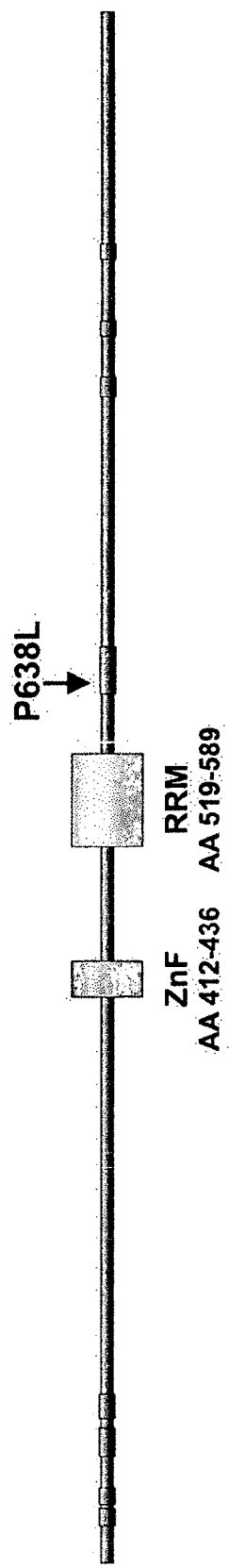

POLYNUCLEOTIDES FOR USE IN MEDICINE

RELATED APPLICATIONS

Figure 1:
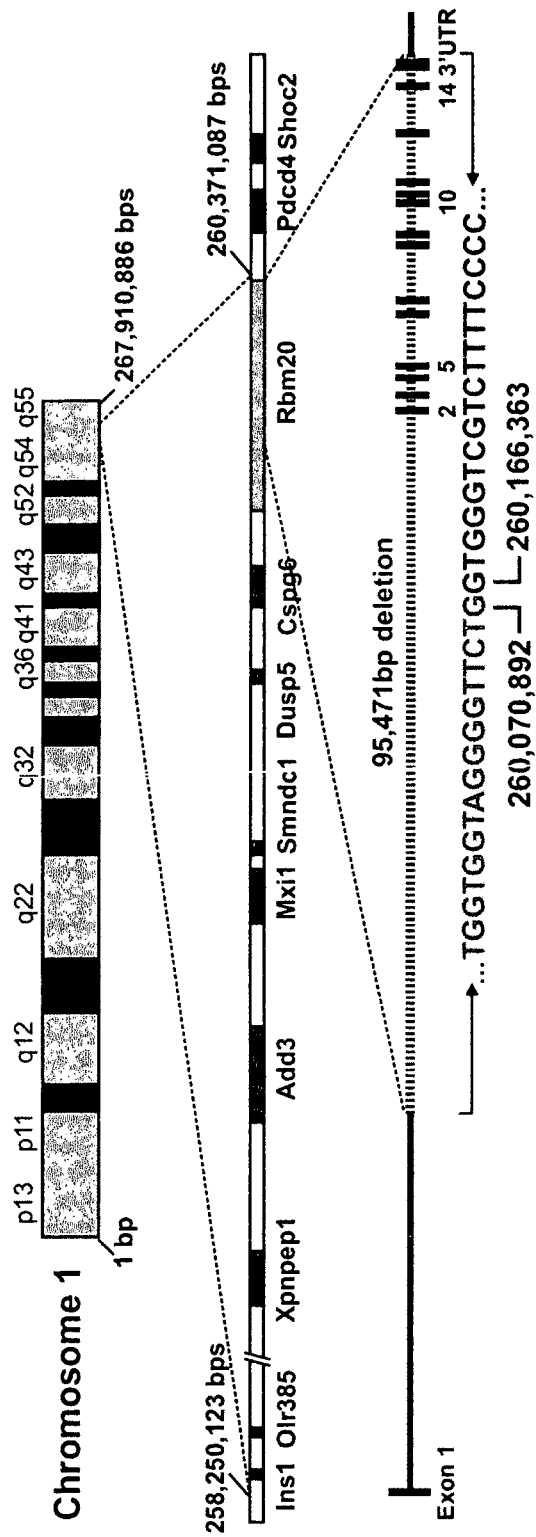

This application claims the benefit of International Patent Application No. PCT/EP2010/003743 filed on Jun. 22, 2010; and U.S. Provisional Patent Application No. 61/219,125 filed on Jun. 22, 2009 the disclosures of each of which are hereby incorporated by reference in their entireties.

TECHNICAL FIELD

The invention pertains to polynuclotides and their uses, including their use in medicine. These polynucleotides can be used to diagnose cardiac diseases, such as cardiomyopathies or sudden cardiac death. Further, the invention pertains to methods for diagnosing a subject suffering from a cardiac disease and to treating such a subject.

The myocardial fetal gene program is downregulated at birth, but reactivates in most forms of human heart failure. Alternative splicing is one major mechanism of this perinatal transition and adjusts cardiac protein isoform expression to the differential requirements of embryonic and postnatal physiology. A paradigmatic example is the titin isoform switch as an adaptive mechanism that determines the biomechanical properties of the heart and thus ventricular filling[1,2]. To explore the molecular basis of this isoform transition and its relevance to cardiac disease, co-segregation analyses using a naturally occurring mutant rat strain deficient in titin splicing were performed[3]. RNA binding motif protein 20 (RBM20) as a putative splice factor that stoichiometrically affects titin isoform expression as part of a coordinated transformation of select cardiac proteins including the ion channel KCNQ1 was identified. A missense mutation in RBM20 at an evolutionarily conserved proline residue (P638L) was identified in a large family with dilated cardiomyopathy that maps to the syntenic human locus (10q25). In both the rodent model and the human family there is evidence of extensive fibrosis, ventricular enlargement and an increased rate of sudden death. The findings establish RBM20 as novel trans-acting factor in the pathogenesis of human heart failure. The co-regulation of sarcomeric proteins and ion-channels in the heart has implications for the adaptation of cardiac function in development and disease.

SUMMARY OF THE INVENTION

The invention provides RNA and DNA polynucleotides selected from the group consisting of: a) polynucleotides encoding the polypeptide RBM20 including a P638L mutation of a human polypeptide RBM20, or a P641L mutation of a rat polypeptide RBM20; b) polynucleotides with a reverse complementary sequence of the polynucleotide of a) above; and c) polynucleotides with at least 50% sequence identity to a polynucleotide of a) or b) above. Also provided are polypeptides encoded by the polynucleotides of a), b) and c) listed above.

The invention further provides a method for diagnosing or monitoring a cardiac disease in a biological sample obtained from a subject, wherein the method includes: determining the presence of a P638L mutation or a P641L mutation in an RBM20 transcript or in an RBM20 protein in a sample from a human or a rat, and deducing from the presence of a P638L mutation or P641L mutation that the subject suffers from a cardiac disease.

The invention also provides a method for treating a subject suffering from a cardiac disease, wherein the method includes increasing the concentration of the wildtype RBM20 mRNA or of the wildtype RBM20 protein in a cardiac cell.

The invention also provides a method for treating a subject suffering from a cardiac disease, wherein the method includes decreasing the concentration of a polynucleotide selected from the group consisting of: a) polynucleotides encoding the polypeptide RBM20 including a P638L mutation of a human polypeptide RBM20, or a P641L mutation of a rat polypeptide RBM20; b) polynucleotides with a reverse complementary sequence of the polynucleotide of a) above; and c) polynucleotides with an identity at least 50% to a polynucleotide of a) or b) above.

The invention further provides a method for treating a subject suffering from a cardiac disease, wherein the method includes decreasing the concentration in a cardiac cell of a polypeptide RBM20 including a P638L mutation of a human polypeptide RBM20, or a P641L mutation of a rat.

The invention also provides a kit for diagnosing, prognosing, or monitoring a cardiac disease in a subject; including a means for: a) determining a P638L mutation in an RBM20 transcript or in an RBM20 protein in a biological sample from a human, or b) a means for determining a P641L mutation in an RBM20 transcript or in an RBM20 protein in a biological sample from a rat.

DESCRIPTION OF THE INVENTION

The invention relates to polynucleotides, the wild type sequences of which are shown below. In particular, the invention refers to RNA binding motif protein 20 (RBM20) polynucleotides that encode for at least one mutation, namely a P638L mutation in human RBM20 or a P641L mutation in rat RBM20.

Homo sapiens RNA binding motif protein 20 (RBM20), polynucleotide, mRNA (NM_001134363.1), translation start codon in bold, SEQ ID NO: 1:

```
CCGGGACCGCCCCTCCCTTGAGCTCTCTCGCCGCGATCCCGGGCGGGTCTCGCCCCGCATGGTGCTGGCA

GCAGCCATGAGCCAGGACGCGGACCCCAGCGGTCCGGAGCAGCCGGACAGAGTTGCCTGCAGTGTGCCTG

GTGCCCGGGCGTCCCCGGCACCCTCCGGCCCGCGAGGGATGCAGCAGCCGCCGCCGCCGCCCCAGCCACC

GCCCCCGCCCCAAGCCGGCCTACCCCAGATCATCCAAAATGCCGCCAAGCTCCTGGACAAGAACCCATTC

TCGGTCAGTAACCCGAACCCTCTGCTTCCTTCACCTGCCAGTCTCCAGCTGGCTCAACTGCAGGCCCAGC

TCACCCTCCACCGGCTGAAGCTGGCACAGACAGCTGTCACCAACAACACTGCAGCCGCCACAGTCCTGAA

CCAAGTCCTCTCCAAAGTGGCCATGTCCCAGCCTCTCTTCAATCAACTGAGGCATCCGTCTGTGATCACT

GGCCCCCACGGCCATGCTGGGGTTCCCCAACATGCTGCAGCCATACCCAGTACCCGGTTTCCCTCTAATG
```

-continued

```
CAATTGCCTTTTCACCCCCAGCCAGACACGAGGCCCCGGACCCTCCATGAACCTTCCCAACCAGCCACC

CAGTGCCATGGTGATGCATCCTTTCACTGGGGTAATGCCTCAGACCCCTGGCCAGCCAGCAGTCATCTTG

GGCATTGGCAAGACTGGGCCTGCTCCAGCTACAGCAGGATTCTATGAGTATGGCAAAGCCAGCTCTGGCC

AGACATATGGCCCTGAAACAGATGGTCAGCCTGGCTTCCTGCCATCCTCGGCCTCAACCTCGGGCAGTGT

GACCTATGAAGGGCACTACAGCCACACAGGGCAGGATGGTCAAGCTGCCTTTTCCAAAGATTTTTACGGA

CCCAACTCCCAAGGTTCACATGTGGCCAGCGGATTTCCAGCTGAGCAGGCTGGGGGCCTGAAAAGTGAGG

TCGGGCCACTGCTGCAGGGCACAAACAGCCAATGGGAGAGCCCCATGGATTCTCGGGCCAAAGCAAGCC

TGATCTCACAGCAGGTCCCATGTGGCCTCCACCCCACAACCAGCCCTATGAGCTGTACGACCCCGAGGAA

CCAACCTCAGACAGGACACCTCCTTCCTTCGGGGGTCGGCTTAACAACAGCAAACAGGGTTTTATCGGTG

CTGGGCGGAGGGCCAAGGAGGACCAGGCGTTGCTATCTGTGCGGCCCCTGCAGGCTCATGAGCTGAACGA

CTTTCACGGTGTGGCCCCCCTCCACTTGCCGCATATCTGTAGCATCTGTGACAAGAAGGTGTTTGATTTG

AAGGACTGGGAGCTGCATGTGAAAGGGAAGCTGCACGCTCAGAAATGCCTGGTCTTCTCTGAAAATGCTG

GCATCCGGTGTATACTTGGTTCGGCAGAGGGAACATTGTGTGCTTCTCCCAACAGCACAGCTGTTTATAA

CCCTGCTGGGAATGAAGATTATGCCTCAAATCTTGGAACATCATACGTGCCCATTCCAGCAAGGTCATTC

ACTCAGTCAAGCCCCACATTTCCTTTGGCTTCTGTGGGGACAACTTTTGCACAGCGGAAAGGGGCTGGCC

GTGTGGTGCACATCTGCAATCTCCCTGAAGGAAGCTGCACTGAGAATGACGTCATTAACCTGGGGCTGCC

CTTTGGAAAGGTCACTAATTACATCCTCATGAAGTCGACTAATCAGGCCTTTTTAGAGATGGCTTACACA

GAAGCTGCACAGGCCATGGTCCAGTATTATCAAGAAAAATCTCCTGTGATCAATGGTGAGAAGTTGCTCA

TTCGGATGTCCAAGAGATACAAGGAATTGCAGCTCAAGAAACCGGGGRAGGCCGTGGCTGCCATCATCCA

GGACATCCATTCCCAGAGGGAGAGGGACATGTTCCGGGAAGCAGACAGATATGGCCCAGAAAGGCCGCGG

TCTCGTAGTCCGGTGAGCCGGTCACTCTCCCCGAGGTCCCACACTCCCAGCTTCACCTCCTGCAGCTCTT

CCCACAGCCCTCCGGGCCCCTCCCGGGCTGACTGGGGCAATGGCCGGGACTCCTGGGAGCACTCTCCCTA

TGCCAGGAGGGAGGAAGAGCGAGACCCGGCTCCCTGGAGGGACAACGGAGATGACAAGAGGGACAGGATG

GACCCCTGGGCACATGATCGCAAACACCACCCCCGGCAACTGGACAAGGCTGAGTTGGACGAGCGACCAG

AAGGAGGGAGGCCCCACCGGGAGAAGTACCCGAGATCTGGGTCTCCCAACCTGCCCCACTCTGTGTCCAG

CTACAAAAGCCGTGAAGACGGCTACTACCGGAAAGAGCCCAAAGCCAAGTGGGACAAGTATCTGAAGCAG

CAGCAGGATGCCCCCGGGAGGTCCAGGAGGAAAGACGAGGCCAGGCTGCGGGAAAGCAGACACCCCCATC

CGGATGACTCAGGCAAGGAAGATGGGCTGGGGCCAAAGGTCACTAGGGCCCCTGAGGGCGCCAAGGCCAA

GCAGAATGAGAAAAATAAAACCAAGAGAACTGATAGAGACCAAGAAGGAGCTGATGATAGAAAAGAAAAC

ACAATGGCAGAGAATGAGGCTGGAAAAGAGGAACAGGAGGGCATGGAAGAAAGCCCTCAATCAGTGGGCA

GACAGGAGAAAGAAGCAGAGTTCTCTGATCCGGAAAACACAAGGACAAAGAAGGAACAAGATTGGGAGAG

TGAAAGTGAGGCAGAGGGGGAGAGCTGGTATCCCACTAACATGGAGGAGCTGGTGACAGTGGACGAGGTT

GGGGAAGAAGAAGATTTTATCGTGGAACCAGACATCCCAGAGCTGGAAGAAATTGTGCCCATTGACCAGA

AAGACAAAATTTGCCCAGAAACATGTCTGTGTGTGACAACCACCTTAGACTTAGACCTGGCCCAGGATTT

CCCCAAGGAAGGAGTCAAGGCCGTAGGGAATGGGGCTGCAGAAATCAGCCTCAAGTCACCCAGAGAACTG

CCCTCTGCTTCCACAAGCTGTCCCAGTGACATGGACGTGGAAATGCCTGGCCTAAATCTGGATGCTGAGC

GGAAGCCAGCTGAAAGTGAGACAGGCCTCTCCCTGGAGGATTCAGATTGCTACGAGAAGGAGGCAAAGGG

AGTGGAGAGCTCAGATGTTCATCCAGCCCCTACAGTCCAGCAAATGTCTTCCCCTAAGCCAGCAGAGGAG

AGGGCCCGGCAGCCAAGCCCATTTGTGGATGATTGCAAGACCAGGGGGACCCCCGAAGATGGGGCTTGTG

AAGGCAGCCCCCTGGAGGAGAAAGCCAGCCCCCCCATCGAAACTGACCTCCAAAACCAAGCTTGCCAAGA
```

-continued

```
AGTGTTGACCCCGGAAAACTCCAGGTACGTGGAAATGAAATCTCTGGAGGTGAGGTCACCAGAGTACACT
GAAGTGGAACTGAAACAGCCCCTTTCTTTGCCCTCTTGGGAACCAGAGGATGTGTTCAGTGAACTTAGCA
TTCCTCTAGGGGTGGAGTTCGTGGTTCCCAGGACTGGCTTTTATTGCAAGCTGTGTGGGCTGTTCTACAC
GAGCGAGGAGACAGCAAAGATGAGCCACTGCCGCAGCGCTGTCCACTACAGGAACTTACAGAAATATTTG
TCCCAGCTGGCCGAGGAGGGCCTCAAGGAGACCGAGGGGGCAGATAGCCCGAGGCCAGAGGACAGCGGAA
TCGTGCCACGCTTCGAAAGGAAAAAGCTCTGATGCTTCTGCTTCTGCTGCTACTGCTGCTGCTGCAAGGT
TGGAAAGGAGAGCTTGCTGAAGTGGGGCCTTCCTGATTCTGGGGACAGGACTAAAGCCTGAGAGGAAGGA
AAACCAAGCAGGGCACATTGCTTGGGCTTGTTCCCAGAGACTCAGTGAAATGCCCCTGATATGTCTCCAG
GAGCAAGTCACCCAGGTGTGTCCAGCCCACTGAGGGTCACCAACTCTCTCCCTGCTGACTCTTGTTTCTC
TCAATCTTTCAATTCGTTTTTCTCTCTTTTCCTCTTGTTCTTTCTCTCCCTCCCTCCTTATGTGCCAAGG
ATCGTTTCCTTTTCACAAAACCCAACTTCTCAGGGATTTTCACAGTGTTTAAATTCTTGGTAGGATATAA
CAGGTCAGGCCTAGCTGAGTCAGGCAAGGAAAAGGTTTAATGGAAACTCCTGGGTCAGGCGAACCCCTGC
AGTGAGTCTACAGCAGTATCTCTGCCTGGTGTCCCATGTATCCCCTGCATGAGGAGCTGAGTCAGGTCTG
CAGTCCTGGTGAGGGGACATCACGGACAATCTGTTGGCAGAGCTGGGAGGGTCTTCATTAACCTCTTCCT
CCAACTGGGCCACCCTTTTGAAAAGCCCCTGTTTTTAATAACTGTTTCATCCTCTCAGTTATTCTAGAAA
TCTGCCAGACTTATGCCTTAAAGTAAAATTAAATGAATTTTAGAGAAGATGAAAAGAGCCCTTCATTTTG
GAAGCTCTGATAAGTTTCCTCCAAACTTATTCCCCTCCTCTTGATTTCAGGAGATGTCAGGGTTTTTCTA
TTCTGGACAATGAATTTGGTACAGAGTCACTGTAATTAAATATAAAAACAGAAGCATCTTCCTCCAGCTA
AAGCAGCAGTTGGCGCGGGCTTAGGTTGAATGCTGGCCTCTCTGCAAAGCACAGCTTTGGCTCGAGAGGC
ACAGCTCCAGGCTGTGGAAAACAGAGTTGTCTTGGGGGTTAAATGAGCTTATTTAAGTCAAGGAAACATC
ATCTGTCCTTGATTCAGCCTTGGTGCCTGCACTCTGGGGTACAACCACCTCACAGTAGGATGGTTTTTAA
ATGGCCCCCAGTTGGGGGAGAAGCTAAGGAAAGAGAAGGCTGCAGATCCAAAGAGTGGCATTGAAGTTT
GCTGGGTGTCTGTAGGTGGACCCTTTCCAGCTGGGCAGATAGTTGAGGGCTCCCTGGGTTTGACTGTATG
TGCAGACTTTGATACCAAAATGTTATGAAAAGTCGTGATTCCCGCTGCTCTTTCTGGTACTGGAGGGTGG
GTACCTTCAGGCTGTGGGGTCTCTAGCCTGATATTCCATTGAAAGGGTGTGGGATAAAGGTGCTGGGGGA
AATGAGGCTCTGCCACAGCCATAGAGAGGCCCTCGGGCAGTTAAGAAGGGAGCCTGGAGCTGTTTTCATG
AGCAGAGATACTCTCCTGAAAGCACCCTTCATAGCTTAGCCCAGGAAAAATAAAACAAGGAAGACAGGTC
ACTCTCCCCTAGGCAGTTCCTGTTGTTTCTGTTCCTGACCTTGGGCAGGCAGACTGAGAAGGGACTGTGT
AGGGTTTTGTTTTGTTTTTTTTCATTTTCCTTTTTATGGCATGTGAGAGCATACTGTACATTCTGTCCTC
TGTACTAATGGAGGAAGGGCAGAGAGATTAGTTCAAGGCTAACATTTTATATCAGGTAACTGAGGCACAC
AAAGGGAACAAATGAAGAACATAAAATGATCACTGTAAACCTGAAAGCACGCAGTCATTGGCAAGGGACA
GGCTCATGGGAGCTGGTGAGAGAGAGCAGTTAAGGCAAGCACCAGGGGAAAGCAGACCAACTTGAACAGA
TGTGATGCGGAGAGGTTGGAAGAAGCAAGAAACCTGAACTCATCATCAGGCTATTAAATAAAATTTATAG
GAGGCTGTTGGTTTGGACTGAGCTCCTGCAATAGGCCCAACAGACCAAAACAAAAGGGAGTCACTCATGT
TGAAGTTCTGTCTTCCAGGAAATCAGGAGAGAGAGAGAGAGAAAGAATAGCCAAATCCCCAAACAGGCCA
GTTTTAACCAGCATGATGAAGTGTCCTTGGTTTTAACCTTTATAAGGAAAGCAGCTTTGAGATGACCAGT
CTGGTTTTTGTTCTTTGTGTCTGCTTTCCTCAGCCCTTTTCTGTCTATAAAGCCAACCTCCTCCGCTCAG
CTCATGGGAACACTCATTCTATTTTATAGAATGACATGTTGCCCAATTCTAGAATCAAAAATAAAGGCCA
ACTAAGATCTTCAAAGTAAATTTGTTGTAATTTTATCTTTTGAGAAGACCATATGGGGGCTGCTGAAAAG
TTGGTATCTCAAATAAAGTCTGAAGATCACGGCTCAGCCCAGATTGTTCCCCTGGCCAACTCCACAGGTT
TGAACCTGGCATTCTGGACACCAGCTATGCCTCCTCCATTTCTCAGAAAACCTTTGATCTTGTGTGTCTT
```

-continued

```
TCTTCCTACTGAAGGGAATTGTGGGGGCAGTTCTTTGGCCTTCTTGCTGAACTTTGCTGGAAATAGCCCA

CAATTTTTATCAGAGGTTAGAACTGTACATTATCAGAGAGACTGGACACTTTATCCCCTAGCAAAGTGGG

AGAAGATTTTACCAGCTCATTCCACTCCACCCTGGCCTTCCCCCACCCCCCATCCCCAGCAGCATTTCCA

TGGAAATCCAGATGGTCGTGTAGTGTTATGGCTCTCTTGTGATAGACTGGCCTTCATATTGGAGAGCTAG

GGAGAGCCCCTGGGAGGGAGAGAGATAAGGCGCTATCTGCCTTCAATCAGAACCTTCGGTTTAAAATCAT

CTAAGAGTCTATACTTGTGTGTACATACGTATTTATTTTTATTTATTTTTATACAATTCCATTGGCATGG

TCCTTCACCGACCCTATGATTTGCACTTTTTATTTCTATGTGTGCCACACACAATGCAGTATTAATGGCA

ACCAGGTAAATATTGATTTATTTTTTAAAGCTTTTCTTCAGTGTTTTGTCAACCATTTCAAAGTGTCTCC

CAAAAAAGGATGCTGAAGAGCAATTGCTCCCTTAAGCAACAGATTCATATTTACCCTGGGTTAATACAAC

AAAAGGCCTGTATAATTGTCTTTTCATTGTTAACACCCAAAATAGCATCTATCTAGACAGTATCCCCAAA

GAATTTGGAAAATCTGATGGTGTGAGCAGCAGCCGTTAGTATCAGGGTTTCCCATTCTTGGACAGTCCGA

GGCTGTGACCTGTTAGATAATTAGATTATACTTGAACTGGACCAGAGTTTGTTTTTTGAATTTATGAGAA

AAACCAAAACACTAAGTTAAGTTTGAACTTGTAAAGTATTGAAATTTGTTGAGTGTCCTATAAATTGTCA

CTACTTTTCCTGATCTGTATAACTGACTGCAAAGTGTTTGTTTTTACAAAAGAGAAAAGAAAAGATTTTT

AATAAAGAGAATTTGAAAGCTGT
```

Rattus norvegicus RNA binding motif protein 20 (predicted) (Rbm20_predicted), polynucleotide, mRNA (XM_220079.4), SEQ ID NO. 2:

```
AAGGGGACTGGGTACAGGGACCCCGGCCAGTGAGCGCCTGTGTTCCGGGACCGCCCCTCCCTCGCGCTCT

TTCGCTGCGAGCCCGGGTCGGTGTCGCCGCGCATGGTGCTGGCTGCAGCCATGAGCCAAGACGCGGATCC

CAGCGGTCCGGAGCAACCCGACAGAGATGCCTGCATTGTGCCTGGTGTTCAAGGGCCCCTGCGCCCCAA

GGCCAGCAAGGGATGCAGCCCCTGCCGCCACCGCTACCGCCACCGCCTCAGCCTCAATCCAGCCTGCCCC

AGATCATCCAAAATGCTGCCAAGCTCCTGGACAAGAACCCCTTCTCCGTCAGTAGCCAGAACCCTCTGCT

CACTTCGCCAGCCAGCGTCCAGCTGGCCCAGATACAGGCCCAGCTCACCCTCCATCGGCTGAAGATGGCA

CAGACCGCAGTCACCAACAACACTGCAGCCGCCACTGTCCTCAACCAAGTCCTCTCCAAAGTGGCCATGT

CCCAGCCTCTCTTCAACCAGCTTCGCCATCCGTCTGTGCTTGGCACCACACATGGCCCTACTGGGGTCTC

CCAGCATGCTGCCACCGTTCCCAGTGCTCACTTTCCCTCAACTGCAATCGCCTTTTCGCCCCCAAGCCAG

GCAGGAGGCCCGGGGCCTTCTGTGAGCCTCCCCAGCCAGCCCCCCAATGCTATGGTAGTGCATACCTTCA

GTGGGGTGGTGCCTCAGACCCCTGCCCAGCCAGCAGTCATCCTAAGCATTGGGAAGGCGGGGCCAACACC

TGCTACTACAGGGTTCTATGACTATGGCAAAGCCAACCCTGGCCAGGCCTATGGTTCTGAAACGGAGGGC

CAGCCGGGCTTCTTGCCAGCCTCGGCGTCAGCCGCAGCATCAGGCGGTGTGACCTATGAAGGACACTATA

GCCACACAGGGCAGGATGGCCAAGCCACCTTTTCTAAAGACTTCTATGGACCCAGTGCCCAAGGGTCACA

TGCAGCAGGTGGGTTCCCAGCTGATCAGGCTGGGAGCATGAAAGGAGACGTCGGTGGGTTGTTGCAAGGT

ACCAACAGCCAGTGGGAGAGGCCCTCTGGGTTCTCTGGCCAGAACAAGGCCGATATTACAGCCGGGCCCG

GTTTGTGGGCTCCACCTGCCAGTCAGCCTTATGAACTATATGATCCTGAGGAGCCTACCTCAGACAGGGC

CCCTCCTGCCTTTGGATCTCGACTTAACAACAGCAAGCAGGGATTCAACTGCTCCTGCCGGCGGACAAAG

GAGGGGCAGGCCATGCTGTCCGTGAGGCCCCTGCAGGGTCATCAACTGAATGACTTCCGAGGCTTGGCTC

CACTCCACCTTCCACATATCTGCAGCATCTGTGACAAGAAGGTGTTTGACCTGAAGGACTGGGAGCTACA

TGTGAAGGGGAAGTTGCATGCCCAGAAATGCCTGCTCTTCTCAGAAAGTGCTGGCCTCCGGAGTATATGT

GCTACAGGAGAAGGGACGCTGTCTGCCTCTGCAAACAGCACAGCTGTTTATAACCCCACTGGAAATGAGG
```

-continued

```
ATTATACCTCAACTCTTGGAACATCATATGCAGCCATTCCAACAAGGGCCTTTGCTCAATCAAACCCCAT

GTTTCCTTCGGCTTCCTCTGGGACAAATTTTGCACAGAGGAAAGGTGCTGGACGAGTTGTGCACATCTGC

AATCTCCCAGAGGGCAGCTGCACGGAGAATGACGTCATCAACCTGGGGCTGCCCTTTGGCAAGGTCACTA

ATTACATCCTTATGAAGTCAACTAATCAGGCTTTCTTGGAGATGGCTTACACAGAAGCTGCTCAAGCTAT

GGTCCAGTACTACCAAGAAAAGCCCGCGCTTATCAATGGCGAGAAGTTACTCATTCGGATGTCCACGAGA

TACAAGGAATTGCAGCTGAAGAAACCTGGGAAAAATGTGGCTGCTATCATCCAGGACATCCACTCCCAAA

GGGAGAGGTGCATGCTCCGGGAAGCTGACAGATATGGTCCAGAGCGACCACGTTCTCGAAGTCCAATGAG

CCGATCGCTCTCCCCGAGATCCCACAGTCCTCCTGGCCCCTCTCGGGCTGATTGGGGCAATGGCCGTGAC

TCCTACGCATGGAGGGACGAGGATCGGGAGACGGTGCCCAGGAGGGAGAACGGGGAAGACAAGAGGGACA

GGTTGGATGTTTGGGCACATGACCGGAAACACTATCCCAGGCAGCTGGACAAAGCCGAGTTGGATGAGCG

ACTCGAAGGAGGGAGGGGCTACCGGGAAAAGTACTTGAAGTCAGGGTCCCCCGGCCCACTCCATTCTGCG

TCTGGCTACAAAGGCCGGGAAGATGGCTACCATCGAAAAGAGACTAAAGCTAAGTTGGACAAACACCCAA

AGCAGCAGCAGCAGGATGTGCCAGGAAGATCCAGGAGGAAAGAAGAGGCGCGACTACGGGAGCCCAGACA

CCCTCACCCAGAGGACTCTGGCAAGGAAGAGGATCTGGAGCCCAAGGTCACTCGGGCCCCCGAGGGTACC

AAGTCCAAGCAAAGTGAGAAAAGTAAAACCAAGAGAGCCGACAGAGACCAAGAAGGAGCTGATGACAAAA

AAGAAGGCCGAGGGGCAGAGAATGAGGCTGGGACTGAGGAACAGGAAGGCATGGAAGAGAGCCCCGCATC

GGTGGGCACACAGCAGGAAGGGACGGAGTCCTCCGATCCAGAAAACACAAGGACAAAGAAGGGACAAGAC

TGTGACAGTGGAAGTGAGCCTGAGGGGGACAACTGGTACCCCACCAACATGGAGGAGCTGGTCACAGTGG

ACGAAGTAGGGGAGGAAGACTTCATCATGGAGCCAGACATACCGGAGCTGGAAGAAATTGTACCCATCGA

CCAGAAAGACAAAATCCTCCCCGAAATATGTCCCTGTGTAACAGCCACCTTAGGTTTGGACTTGGCCAAA

GACTTCACCAAGCAGGGAGAGACCCTAGGGAACGGAGACGCAGAACTCAGCCCGAAGCTGCCCGGACAAG

TGCCGTCTACTTCCACAAGCTGTCCCAATGACACGGACATGGAGATGGCTGGCCTAAATCTGGATGCTGA

GCGGAAGCCAGCTGAAAGCGAGACAGGCCTCTCACCGGAGGTCTCAAATTGCTACGAGAAGGAGGCGAGA

GGAGCGGAGGGCTCAGATGTGCGTCTGGCCCCTGCAGCCCAGCGAATGTCCTCCCCTCAGCCAGCAGATG
```

The invention also relates to polynucleotide sequences that are reverse complementary to a sequence of RBM20 (Homo sapiens and Rattus norvegicus) comprising the P638L mutation (Homo sapiens) or comprising the P641L mutation (Rattus norvegicus).

Further embodiments of the invention are polynucleotide sequences that have at least 50%, at least 60%, at least 70%, at least 80%, at least 90%, at least 95%, at least 98%, at least 99% identity to the polynucleotide sequences mentioned above (i.e. the wildtype coding sequence of RBM20 comprising a P638L mutation (Homo sapiens) or comprising the P641L mutation (Rattus norvegicus), possibly together with other mutations.

Preferably, the mutated polynucleotide is an isolated and/or purified molecule. In a preferred embodiment, it can be used in medicine. Preferably, it can be used for diagnosing, prognosing, and/or monitoring the state, i.e. the progress or improvement of a cardiac disease in a subject, which is preferably a human.

The polynucleotide can be selected from the group consisting of DNA and RNA.

The invention also relates to polypeptides (proteins) as shown below with a P638L mutation in human RBM20 or with a P641L mutation in rat RBM20 (shown are the wild type sequences):

Homo sapiens RNA binding motif protein 20, polypeptide (ref|NP_001127835.1), P638 in bold, SEQ ID NO. 3:

```
MVLAAAMSQDADPSGPEQPDRVACSVPGARASPAPSGPRGMQQPPPPPQPPPPPQAGLPQIIQNAAKLLD

KNPFSVSNPNPLLPSPASLQLAQLQAQLTLHRLKLAQTAVTNNTAAATVLNQVLSKVAMSQPLFNQLRHP

SVITGPHGHAGVPQHAAAIPSTRFPSNAIAFSPPSQTRGPGPSMNLPNQPPSAMVMHPFTGVMPQTPGQP

AVILGIGKTGPAPATAGFYEYGKASSGQTYGPETDGQPGFLPSSASTSGSVTYEGHYSHTGQDGQAAFSK

DFYGPNSQGSHVASGFPAEQAGGLKSEVGPLLQGTNSQWESPHGFSGQSKPDLTAGPMWPPPHNQPYELY

DPEEPTSDRTPPSFGGRLNNSKQGFIGAGRRAKEDQALLSVRPLQAHELNDFHGVAPLHLPHICSICDKK
```

-continued

VFDLKDWELHVKGKLHAQKCLVFSENAGIRCILGSAEGTLCASPNSTAVYNPAGNEDYASNLGTSYVPIP

ARSFTQSSPTFPLASVGTTFAQRKGAGRVVHICNLPEGSCTENDVINLGLPFGKVTNYILMKSTNQAFLE

MAYTEAAQAMVQYYQEKSAVINGEKLLIRMSKRYKELQLKKPGKAVAAIIQDIHSQRERDMFREADRYGP

ERPRSRSPVSRSLSPRSHTPSFTSCSSSHSPPGPSRADWGNGRDSWEHSPYARREEERDPAPWRDNGDDK

RDRMDPWAHDRKHHPRQLDKAELDERPEGGRPHREKYPRSGSPNLPHSVSSYKSREDGYYRKEPKAKWDK

YLKQQQDAPGRSRRKDEARLRESRHPHPDDSGKEDGLGPKVTRAPEGAKAKQNEKNKTKRTDRDQEGADD

RKENTMAENEAGKEEQEGMEESPQSVGRQEKEAEFSDPENTRTKKEQDWESESEAEGESWYPTNMEELVT

VDEVGEEEDFIVEPDIPELEEIVPIDQKDKICPETCLCVTTTLDLDLAQDFPKEGVKAVGNGAAEISLKS

PRELPSASTSCPSDMDVEMPGLNLDAERKPAESETGLSLEDSDCYEKEAKGVESSDVHPAPTVQQMSSPK

PAEERARQPSPFVDDCKTRGTPEDGACEGSPLEEKASPPIETDLQNQACQEVLTPENSRYVEMKSLEVRS

PEYTEVELKQPLSLPSWEPEDVFSELSIPLGVEFVVPRTGFYCKLCGLFYTSEETAKMSHCRSAVHYRNL

QKYLSQLAEEGLKETEGADSPRPEDSGIVPRFERKKL

Rattus norvegicus RNA binding motif protein 20 (Rbm20), polypeptide (XM_220079.4), P641 in bold, SEQ ID NO. 4:

MVLAAAMSQDADPSGPEQPDRDACIVPGVQGPPAPQGQQGMQPLPPPLPPPPQPQSSLPQIIQNAAKLLD

KNPFSVSSQNPLLTSPASVQLAQIQAQLTLHRLKMAQTAVTNNTAAATVLNQVLSKVAMSQPLFNQLRHP

SVLGTTHGPTGVSQHAATVPSAHFPSTAIAFSPPSQAGGPGPSVSLPSQPPNAMVVHTFSGVVPQTPAQP

AVILSIGKAGPTPATTGFYDYGKANPGQAYGSETEGQPGFLPASASAAASGGVTYEGHYSHTGQDGQATF

SKDFYGPSAQGSHAAGGFPADQAGSMKGDVGGLLQGTNSQWERPSGFSGQNKADITAGPGLWAPPASQPY

ELYDPEEPTSDRAPPAFGSRLNNSKQGFNCSCRRTKEGQAMLSVRPLQGHQLNDFRGLAPLHLPHICSIC

DKKVFDLKDWELHVKGKLHAQKCLLFSESAGLRSICATGEGTLSASANSTAVYNPTGNEDYTSTLGTSYA

AIPTRAFAQSNPMFPSASSGTNFAQRKGAGRVVHICNLPEGSCTENDVINLGLPFGKVTNYILMKSTNQA

FLEMAYTEAAQAMVQYYQEKPALINGEKLLIRMSTRYKELQLKKPGKNVAAIIQDIHSQRERCMLREADR

YGPERPRSRSPMSRSLSPRSHSPPGPSRADWGNGRDSYAWRDEDRETVPRRENGEDKRDRLDVWAHDRKH

YPRQLDKAELDERLEGGRGYREKYLKSGSPGPLHSASGYKGREDGYHRKETKAKLDKHPKQQQQDVPGRS

RRKEEARLREPRHPHPEDSGKEEDLEPKVTRAPEGTKSKQSEKSKTKRADRDQEGADDKKEGRGAENEAG

TEEQEGMEESPASVGTQQEGTESSDPENTRTKKGQDCDSGSEPEGDNWYPTNMEELVTVDEVGEEDFIME

PDIPELEEIVPIDQKDKILPEICPCVTATLGLDLAKDFTKQGETLGNGDAELSPKLPGQVPSTSTSCPND

TDMEMAGLNLDAERKPAESETGLSPEVSNCYEKEARGAEGSDVRLAPAAQRMSSPQPADERAQQSSPFLD

DCKARGSPEDGPHEVSPLEEKASPTTESDLQSQACQENSRYTETRSLNSRSPEFTEAELKEPLSLPSWEP

EVFSELSIPLGVEFVVPRTGFYCKLCGLFYTSEEAAKVSHCRSTVHYRNLQKYLSQLAEEGLKETEGVDS

PSPERSGIGPHLERKKL

Shown below is the sequence of a homo sapiens RNA binding motif protein 20 polypeptide (protein) with a P638L mutation (bold), SEQ ID NO. 5:

MVLAAAMSQDADPSGPEQPDRVACSVPGARASPAPSGPRGMQQPPPPQPPPPQAGLPQIIQNAAKLLD

KNPFSVSNPNPLLPSPASLQLAQLQAQLTLHRLKLAQTAVTNNTAAATVLNQVLSKVAMSQPLFNQLRHP

SVITGPHGHAGVPQHAAAIPSTRFPSNAIAFSPPSQTRGPGPSMNLPNQPPSAMVMHPFTGVMPQTPGQP

AVILGIKTGPAPATAGFYEYGKASSGQTYGPETDGQPGFLPSSASTSGSVTYEGHYSHTGQDGQAAFSK

DFYGPNSQGSHVASGFPAEQAGGLKSEVGPLLQGTNSQWESPHGFSGQSKPDLTAGPMWPPPHNQPYELY

```
DPEEPTSDRTPPSFGGRLNNSKQGFIGAGRRAKEDQALLSVRPLQAHELNDFHGVAPLHLPHICSICDKK

VFDLKDWELHVKGKLHAQKCLVFSENAGIRCILGSAEGTLCASPNSTAVYNPAGNEDYASNLGTSYVPIP

ARSFTQSSPTFPLASVGTTFAQRKGAGRVVHICNLPEGSCTENDVINLGLPFGKVTNYILMKSTNQAFLE

MAYTEAAQAMVQYYQEKSAVINGEKLLIRMSKRYKELQLKKPGKAVAAIIQDIHSQRERDMFREADRYGP

ERPRSRSLVSRSLSPRSHTPSFTSCSSSHSPPGPSRADWGNGRDSWEHSPYARREEERDPAPWRDNGDDK

RDRMDPWAHDRKHHPRQLDKAELDERPEGGRPHREKYPRSGSPNLPHSVSSYKSREDGYYRKEPKAKWDK

YLKQQQDAPGRSRRKDEARLRESRHPHPDDSGKEDGLGPKVTRAPEGAKAKQNEKNKTKRTDRDQEGADD

RKENTMAENEAGKEEQEGMEESPQSVGRQEKEAEFSDPENTRTKKEQDWESESEAEGESWYPTNMEELVT

VDEVGEEEDFIVEPDIPELEEIVPIDQKDKICPETCLCVTTTLDLDLAQDFPKEGVKAVGNGAAEISLKS

PRELPSASTSCPSDMDVEMPGLNLDAERKPAESETGLSLEDSDCYEKEAKGVESSDVHPAPTVQQMSSPK

PAEERARQPSPFVDDCKTRGTPEDGACEGSPLEEKASPPIETDLQNQACQEVLTPENSRYVEMKSLEVRS

PEYTEVELKQPLSLPSWEPEDVFSELSIPLGVEFVVPRTGFYCKLCGLFYTSEETAKMSHCRSAVHYRNL

QKYLSQLAEEGLKETEGADSPRPEDSGIVPRFERKKL
```

Shown below is the sequence of a rattus norvegicus RNA binding motif protein 20 polypeptide (protein) with a P641L mutation (bold), SEQ ID NO. 6:

```
MVLAAAMSQDADPSGPEQPDRDACIVPGVQGPPAPQGQQGMQPLPPPLPPPPQPQSSLPQIIQNAAKLLD

KNPFSVSSQNPLLTSPASVQLAQIQAQLTLHRLKMAQTAVTNNTAAATVLNQVLSKVAMSQPLFNQLRHP

SVLGTTHGPTGVSQHAATVPSAHFPSTAIAFSPPSQAGGPGPSVSLPSQPPNAMVVHTFSGVVPQTPAQP

AVILSIGKAGPTPATTGFYDYGKANPGQAYGSETEGQPGFLPASASAAASGGVTYEGHYSHTGQDGQATF

SKDFYGPSAQGSHAAGGFPADQAGSMKGDVGGLLQGTNSQWERPSGFSGQNKADITAGPGLWAPPASQPY

ELYDPEEPTSDRAPPAFGSRLNNSKQGFNCSCRRTKEGQAMLSVRPLQGHQLNDFRGLAPLHLPHICSIC

DKKVFDLKDWELHVKGKLHAQKCLLFSESAGLRSICATGEGTLSASANSTAVYNPTGNEDYTSTLGTSYA

AIPTRAFAQSNPMFPSASSGTNFAQRKGAGRVVHICNLPEGSCTENDVINLGLPFGKVTNYILMKSTNQA

FLEMAYTEAAQAMVQYYQEKPALINGEKLLIRMSTRYKELQLKKPGKNVAAIIQDIHSQRERCMLREADR

YGPERPRSRSLMSRSLSPRSHSPPGPSRADWGNGRDSYAWRDEDRETVPRRENGEDKRDRLDVWAHDRKH

YPRQLDKAELDERLEGGRGYREKYLKSGSPGPLHSASGYKGREDGYHRKETKAKLDKHPKQQQQDVPGRS

RRKEEARLREPRHPHPEDSGKEEDLEPKVTRAPEGTKSKQSEKSKTKRADRDQEGADDKKEGRGAENEAG

TEEQEGMEESPASVGTQQEGTESSDPENTRTKKGQDCDSGSEPEGDNWYPTNMEELVTVDEVGEEDFIME

PDIPELEEIVPIDQKDKILPEICPCVTATLGLDLAKDFTKQGETLGNGDAELSPKLPGQVPSTSTSCPND

TDMEMAGLNLDAERKPAESETGLSPEVSNCYEKEARGAEGSDVRLAPAAQRMSSPQPADERAQQSSPFLD

DCKARGSPEDGPHEVSPLEEKASPTTESDLQSQACQENSRYTETRSLNSRSPEFTEAELKEPLSLPSWEP

EVFSELSIPLGVEFVVPRTGFYCKLCGLFYTSEEAAKVSHCRSTVHYRNLQKYLSQLAEEGLKETEGVDS

PSPERSGIGPHLERKKL
```

Further embodiments of the invention are polypeptide sequences that have at least 50%, at least 60%, at least 70%, at least 80%, at least 90%, at least 95%, at least 98%, at least 99% identity and/or homology to the polypeptide sequences mentioned above (i.e. the wildtype sequence of RBM20 polypeptide comprising a P638L or P641L mutation).

When referring to a wildtype sequence of RBM20 polypeptide comprising a P638L (or P641L) mutation, the polypeptide may comprise further mutations than the P638L or P641L mutation. Further mutations may be chosen from the group consisting of: R634Q, R636S, R636H, and S637G which are also indicative for a cardiac disease in a subject. Additional mutations than the ones mentioned may also be present in the polypeptide.

Preferably, the mutated polypeptide is an isolated and/or purified molecule. In a preferred embodiment, it is used in medicine, such as for diagnosing, prognosing, and/or monitoring a cardiac disease in a subject, which is preferably a human.

The invention also relates to a method for diagnosing, prognosing, and/or monitoring a cardiac disease in a biological sample obtained from a human subject, comprising
determining the presence or absence of a P638L mutation in a RBM20 transcript or in a RBM20 protein in a sample, and
deducing from the presence of a P638L mutation that the subject suffers from a cardiac disease.

If the subject is a rat, the presence or absence of a P641L mutation is determined.

The invention further relates to a method for preparing an RNA expression profile, a DNA expression profile or a protein expression profile that is indicative of the presence or absence of a cardiac disease in a human subject, comprising isolating RNA, DNA or protein from a biological sample obtained from a subject, and
determining the presence or absence of a P638L mutation in a RBM20 transcript, in a RBM20 gene or in a RBM20 protein in the sample, and
deducing from the presence of a P638L mutation that the subject suffers from a cardiac disease.

If the subject is a rat, the presence or absence of a P641L mutation is determined.

The cardiac disease can be selected from the group consisting of cardiomyopathy and Sudden Cardiac Death (SCD). The cardiomyopathy can be selected from the group consisting of restrictive cardiomyopathy (RCM), dilated cardiomyopathy (DCM), hypertrophic cardiomyopathy (HCM), arrhythmogenic right ventricular cardiomyopathy (ARVC), and fibrotic heart diseases. The Sudden Cardiac Death (SCD) can be selected from the group consisting of arrhythmia related death and ventricular conduction related death.

The invention further relates to a kit for diagnosing, prognosing, and/or monitoring a cardiac disease in a subject, comprising a means for determining a P638L mutation (human subject) or a P641L mutation (rat) in a RBM20 transcript or in a RBM20 protein in a biological sample.

The means for determining a P638L mutation or a P641L mutation is selected from the group consisting of a probe for detecting at least one of the mutations, and a primer for detecting at least one of the mutations in an amplification reaction (PCR, LCR, RTPCR, etc.) and/or in a sequencing reaction. A person of skill in the art can make such means based on the description provided herein together with his general knowledge.

The invention further relates to a microarray for diagnosing, prognosing, and/or monitoring a cardiac disease in a subject, comprising a probe for determining a P638L mutation (human) or a P641L mutation (rat) in a RBM20 transcript in a biological sample.

In this treatment method, the concentration of wildtype RBM20 (i.e. of the mRNA or the protein) in a cardiac cell is increased such that the concentration of the wildtype RBM20 (i.e. of the mRNA or the protein) in the cardiac cell is increased as measured by any suitable method, e.g. PRC or Western blot before and after the treatment. Alternatively, an mRNA molecule with a mutation described herein can be selectively removed in a cell using antisense RNA or siRNA molecules, as known in the art.

Such concentration reduction can be performed with siRNA (s159852, sense 5'-GCCUUUGGAUCUCGACUUAtt-3' SEQ ID NO. 7, antisense 5'-UAAGUCGAGUAC-CAAAGGCag-3' SEQ ID NO. 8; or s159853, Sense 5'-CG-UUCUCGAAGUCCAAUGAtt-3' SEQ ID NO. 9, antisense 5'-UCUUGGACUUCGAGAACGtg-3' SEQ ID NO. 10) (Ambion) designed for inhibition of RBM20 (human, rat, and mouse). Alternatively a small molecule, peptide, chemical, protein, or polynucleotide that interferes with RBM20 expression or binds RBM20-RNA or RBM20-protein or interferes with its function is applied to exert a therapeutic effect. The small molecule might be rationally designed from the RBM20/RNA structure, or screened from a small-molecule library, the protein might be a synthetic or naturally occurring RNA binding protein (or motive), a transcription factor, and the polynucleotide might be a single stranded DNA, RNA, or a variation or combination thereof.

A pharmaceutical composition for treating cardiac diseases comprises RBM20 in the form of an RNA encoding for wildtype RBM20, e.g. an mRNA, or a wildtype protein for delivery into a cell of a subject in need thereof. An alternative pharmaceutical composition comprises an antisense RNA or siRNA molecules to decrease the concentration of wildtype RBM20 (i.e. of the mRNA or the protein) in a cardiac cell in need thereof. This includes siRNAs such as s159852, sense 5'-GCCUUUGGAUCUCGACUUAtt-3' SEQ ID NO. 7, antisense 5'-UAAGUCGAGUACCAAAGGCag-3'SEQ ID NO. 8; or s159853, Sense 5'-CGUUCUCGAAGUCCAAUGAtt-3' SEQ ID NO. 9, antisense 5'-UCAUUGGACUUC-GAGAACGtg-3' SEQ ID NO. 10.

The invention can also be applied to other organisms that humans and rats. A person of skill in the art is able to determine mutations for other organisms that are homologous to the mutations of the invention as described herein.

FIGURES

FIG. 1

Loss of RBM20 causes a shift in titin isoform expression. (a) In a splice deficient rat strain, the QTL from a backcross to Brown-Norway was mapped. Based on 16 affected animals, the locus was assigned to a 2.1 Mbps interval on the long arm of chromosome 1 (1q55). Sequencing of all known genes included in the interval revealed a 95 kb deletion that exclusively affects the RBM20 gene eliminating all exons but exon 1. (b) The deletion was confirmed by southern-blot of genomic DNA with the loss of a 3 kb internal HindIII fragment in the homozygotes (−/−) and a reduced signal in the heterozygotes (+/−) as compared to the wildtype (+/+). (c) RBM20 RNA levels normalized to 18S and wildtype levels reflect the changes documented by Southern blot with 24% reduction in the heterozygote and no expression in the homozygote (<1%). N=9. (d) Transfection of HL-1 cells that express a long titin variant (N2BA) and a shorter titin isoform (N2B) were mock-transfected (−), transfected with a nonsense siRNA (NS), and two different siRNAs directed against RBM20. The siRNA—treated cells did no longer splice titin to express the N2B isoform as compared to the controls (—and NS).

FIG. 2

Signs of cardiomyopathy and sudden death in RBM20 deficient rats. (a, b) Left ventricular diameter in diastole (LVDd) as determined by echocardiography was increased in both heterozygote and homozygote mutants as a sign of dilated cardiomyopathy (P<0.05; N=15). Changes in LV diameter in systole (LVDs) and fractional shortening (FS), a parameter of contractile function, did not reach statistical significance. (c) Subendocardial fibrosis was present in heterozygote mutants (+/−) as indicated by the trichrome staining (blue). The fibrotic area was increased and compacted in the homzygotes. Sizebar=100 μm. (d) Interstitial fibrosis was significantly increased in LV from heterozgotes (13% fibrotic area) and homozygotes (31%) as compared to wildtype hearts (3%). N=13. (e) Starting from 10 months of age there was an increase in sudden death in both heterozygote and homozygote animals with 14% and 17%, respectively vs. 2% in wildtype controls by 18 months of age. Log-rank (Mantel-Cox) test P=0.03; N=130.

FIG. 3

RBM20 affects splicing of a subset of genes associated with cardiomyopathy, fibrosis, and sudden death. (a, b) Among the 67 genes identified as differentially spliced 59 known genes were categorized by localization and function. The majority encoded cytosolic proteins (35%) with 58% of the total involved in signal transduction or metabolism. The sarcomere category (7%) included the known cardiomyopathy genes titin (Ttn), obscurin (Obscn), and myozenin 2 (Myoz2).

FIG. 4

RBM20 dependent splicing is restricted to select exons within target genes. (a-c) Exon analysis by ANOVA (black curve) and splicing indexes (heatmap) of each probe sets representing exons of titin, obscurin, KcnQ1, and the RBM20 independent control Car. The splice index (SI) is plotted as a heatmap using a scale from red (SI −5)=higher levels in wildtype (spliced out) over grey=similar levels as in wildtype (no alternative splicing) to blue (SI 5)=higher level in affected animals (spliced in). The wildtype vs. homozygote SI (−/−) is provided at the top, the wild type vs. heterozygote SI (+/−) at the bottom. The majority of splice events results from increased exon expression in the knockout (blue). Significance levels at P=0.05 (*) and P=0.01 (**) are indicated (N=3 per group). (a) Titin is predominantly spliced in the immunoglobulin-rich region located between N2B and N2A and the elastic PEVK region. The 5' and 3' regions are unaffected as indicated by the p-values <0.05 and the gray shading of the heatmap. (b) In obscurin a small region comprising 2 exons is spliced out by RBM20 (gray line, blue-staining in both +/− and −/− accentuated in the latter). (c) Splicing of the Kcnq1 3' region depends on RBM20 with 6 consecutive probesets representing three exons (gray line, blue). (d) Alternative splicing of titin, obscurin, and Kcnq1 was confirmed by RT-PCR with reduced splicing (as indicated by increased expression levels of the alternatively spliced exons) in heterozygotes and accentuated in homozygote RBM20 deficient rats. CAR was used as a control with known alternative splicing, but independent on RBM20.

FIG. 5

The splice defect maps to the long arm of rat chromosome 1. Affected animals on a mixed Sprague Dawley/Fisher F344 background (SD/F) were backcrossed with Brown Norway rats (BN). (a) With FDR (False Discovery Rate) set to 0.05, linkage is restricted to a 2.1 Mbps interval on chromosome 1 (b—black dot), that includes 3 SNPs with shared heterozygosity in all 16 animals indicated by the dashed gray lines (c). Based on the location of the flanking SNPs the locus containing the candidate gene was assigned to Chr.1: 258,250,123 to 260,371,087 bps.

FIG. 6

Cosegregation of the titin splice defect with the deletion in RBM20. Affected animals on a mixed Sprague Dawley/Fisher F344 background (SD/F) were backcrossed with Fisher F334 (a) or Brown Norway rats (b). Genotypes of 191 animals are indicated as WT for wildtype and HET for heterozygote. All 86 affected rats expressing the long titin isoform were heterozygous for the deletion. Animals that were used for genetic mapping are labeled with a black dot.

FIG. 7

RBM20 in human DCM. (a) Cosegregation of the RBM20 mutation P638L in a family with DCM and sudden death that maps to 10q25 (b) RBM20 domain structure with regions of low complexity shown as gray rings, the Zink-Finger domain (ZnF) in dark (blue), and the RNA recognition motive (RRM) in light (yellow). The P638L mutation detected in the DCM50 family is outside the main functional domains. (c) The phylogenetic tree shows the conservation of the mutant region of RBM20 from human (homo) to zebrafish (danio). Amino acids mutated in the DCM patients analyzed are indicated at position 638. (d) After transfection of tagged mutant (mut) and wildtype Rbm20 (wt) protein levels of the proline-to-leucine mutant were reduced. Control cells were not transfected. (e) Normalization of protein expression to Rbm20 mRNA indicates a posttranscriptional effect. Wildtype Rbm20 protein to RNA levels were set as 1 (n=3 per group).

FIG. 8

Expression of individual RBM20 exons. The GeneChip ST Exon array signal intensities for wildtype (light grey), heterozogote (50% grey) and homozogote (dark grey) were plotted along the UCSC exon-structure (UCSC known genes—http://genomes.ucsc.edu) with genomic position indicated on the vertical axis in Mbps. The expression data reflect the underlying deletion that eliminates all exons but E1 of RBM20. Signal intensities for homozygotes approach background levels, while heterozygotes display intermediate signal levels. N=3 per genotype; asterisks indicate significance (F-Test, P<0.5).

FIG. 9

Alternative splicing of titin depends on RBM20. Comparison of titin exon expression in wildtype, heterozygote, and homozygote RBM20 deficient rats. Probesets with increased RBM20 dependent splicing were localized to the region containing tandem Ig-like domains and the PEVK region (brackets). Most affected probesets were downregulated in both heterozygous and homozygous animals. N=3 per genotype; asterisks indicate significance (F-Test, P<0.5).

FIG. 10

Alternative splicing of Kcnq1 depends on RBM20. Comparison of titin exon expression in wildtype, heterozygote, and homozygote rats. The dominant effect of RBM20 on the 3' region of Kcnq1 is reflected in the significant expression changes between genotypes that affect all 5 probesets located in the last 3 exons. Differences in probeset 8 are not consistent with neighboring probesets within the same exon and are therefore not considered alternative splicing. N=3 per genotype; asterisks indicate significance (F-Test, P<0.5).

FIG. 11

The developmental switch in titin isoform expression is correlated with RBM20 expression in F344 rats. (a) RBM20 transcript levels are increased >2-fold after birth (E18—embryonic day 18; P1—postnatal day 1). (b) Titin splicing as indicated by the expression-ratio of the spliced to unspliced exon-pair (primers indicated in FIG. 4) is reduced after birth and consistent with increased RBM20 expression. Similar isoform transition from embryonic to adult with increased splicing in the adult was found for Obscurin (c) and KcnQ1 (d). (e) The Coxsackievirus and Adenovirus Receptor (CAR) was used as a control with known splicing of the 3'-region that is independent of RBM20. N=4 per group; dCT data are tested for significance by 2 way ANOVA with Bonferroni pot hoc test. $P<0.05 =*; p<0.01=; p<0.001=*$.

EXAMPLES

The mammalian heart adapts to gradual alterations in cardiovascular physiology at birth and these events are associated with widespread changes in gene expression and in the potential for myocyte proliferation. The coordinated regulation of this critical transition in both normal development and in disease is poorly understood, but re-expression of the socalled fetal gene program is a central component of myocardial hypertrophy and is found in a broad range of disease states leading to heart failure. Here, a naturally occurring rat strain deficient in titin splicing with persistent expression of the larger embryonic titin isoform[3] was used to elucidate the molecular basis of perinatal isoform switching and identified a factor that coordinates the splicing of multiple genes involved in the adaptation of cardiac function.

Titin is a giant sarcomeric protein that determines the structure and biomechanical properties of striated muscle. Both posttranslational modification and alternative splicing tune titin based passive tension and enable efficient ventricular filling[4,5]. Titin phosphorylation in response to adrenergic stimulation has been attributed to a direct effect of protein kinase A (PKA) on the elastic N2B region[4], while the factors that determine titin's alternative splicing has so far remained elusive.

Figure 1B:
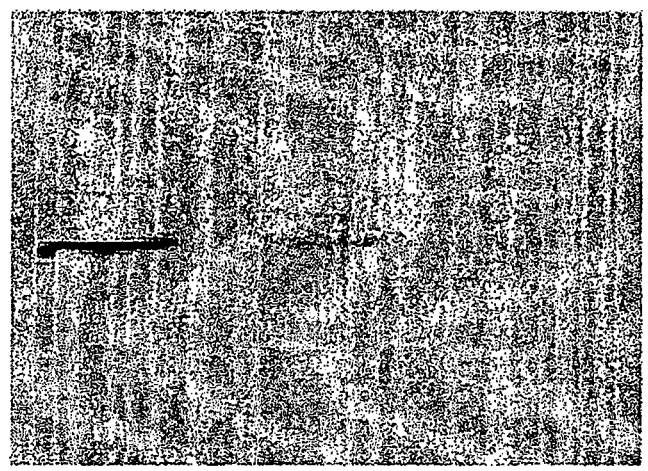
Figure 1C:
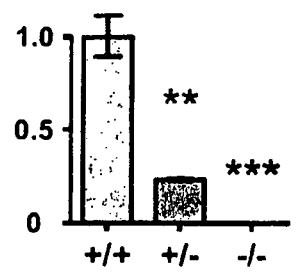
Figure 1D:
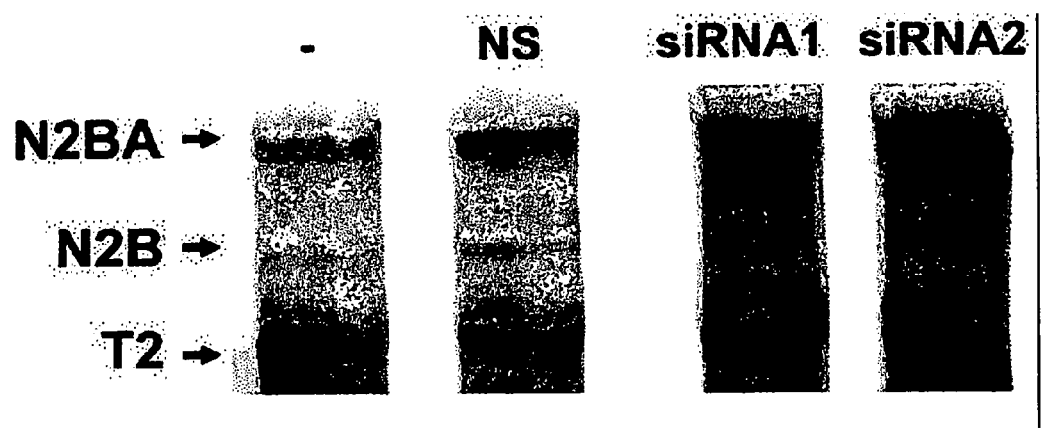
Figure 2A:
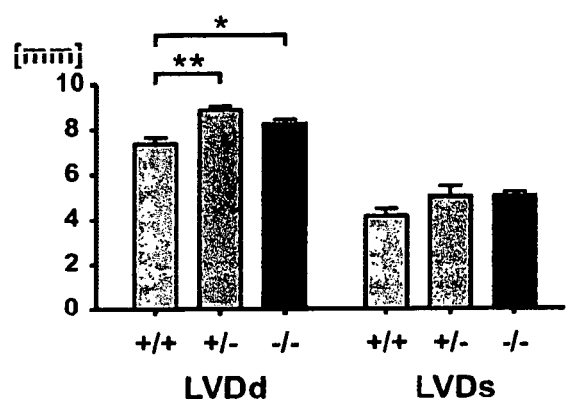
Figure 2B:
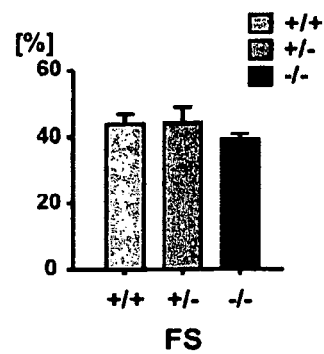
Figure 2C:
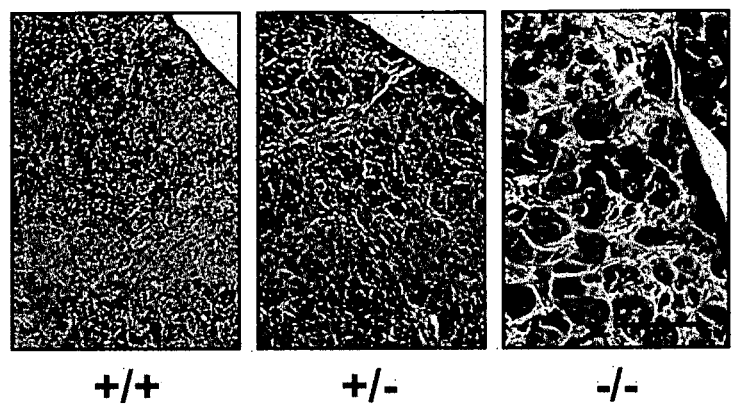
Figure 2D:
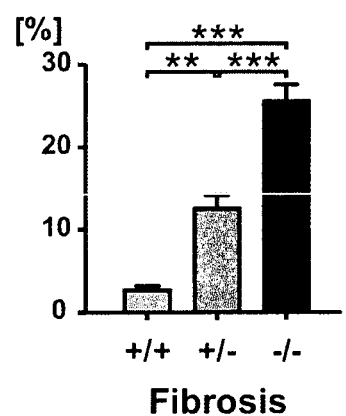
Figure 2E:
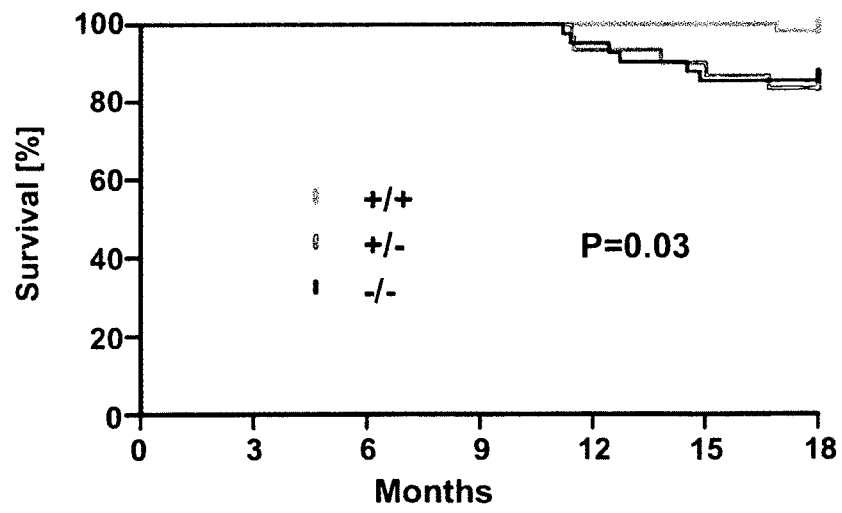
Figure 5A:
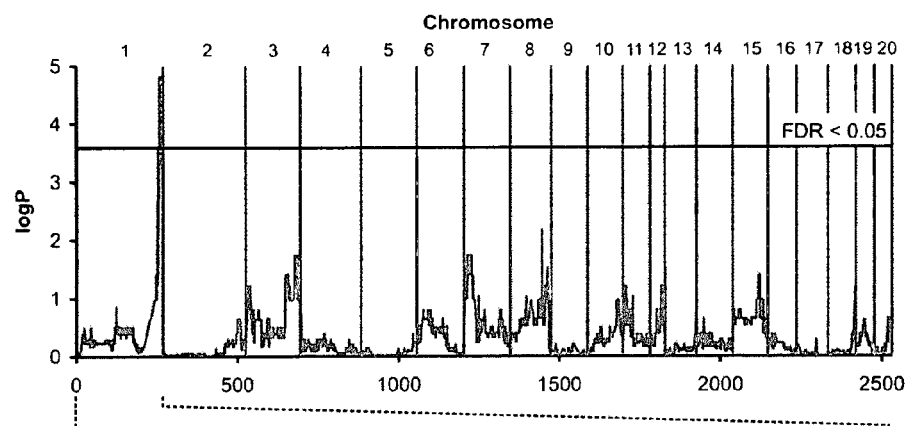
Figure 5B:
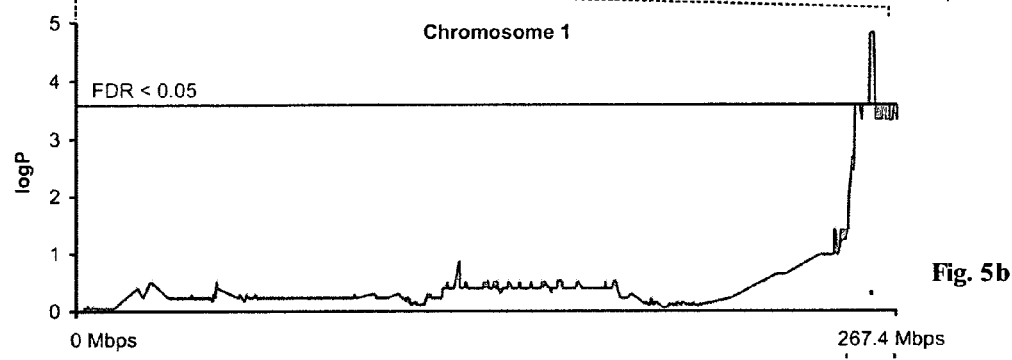
Figure 5C:
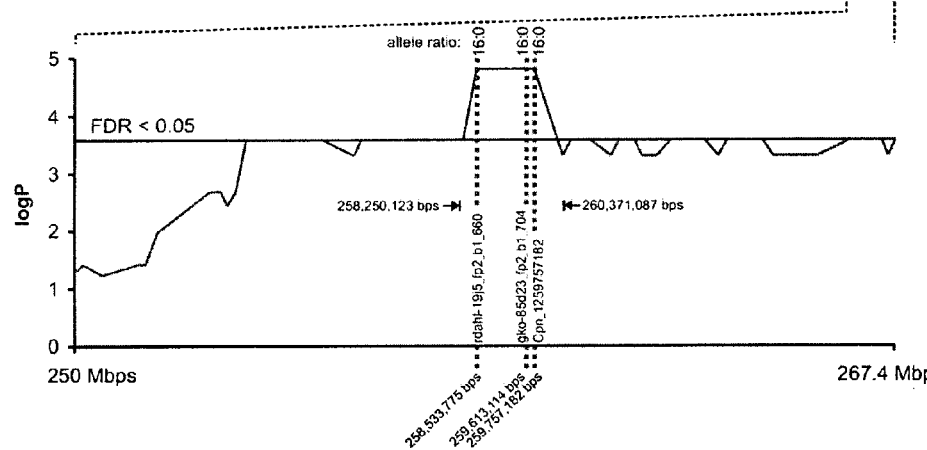
Figure 6A:
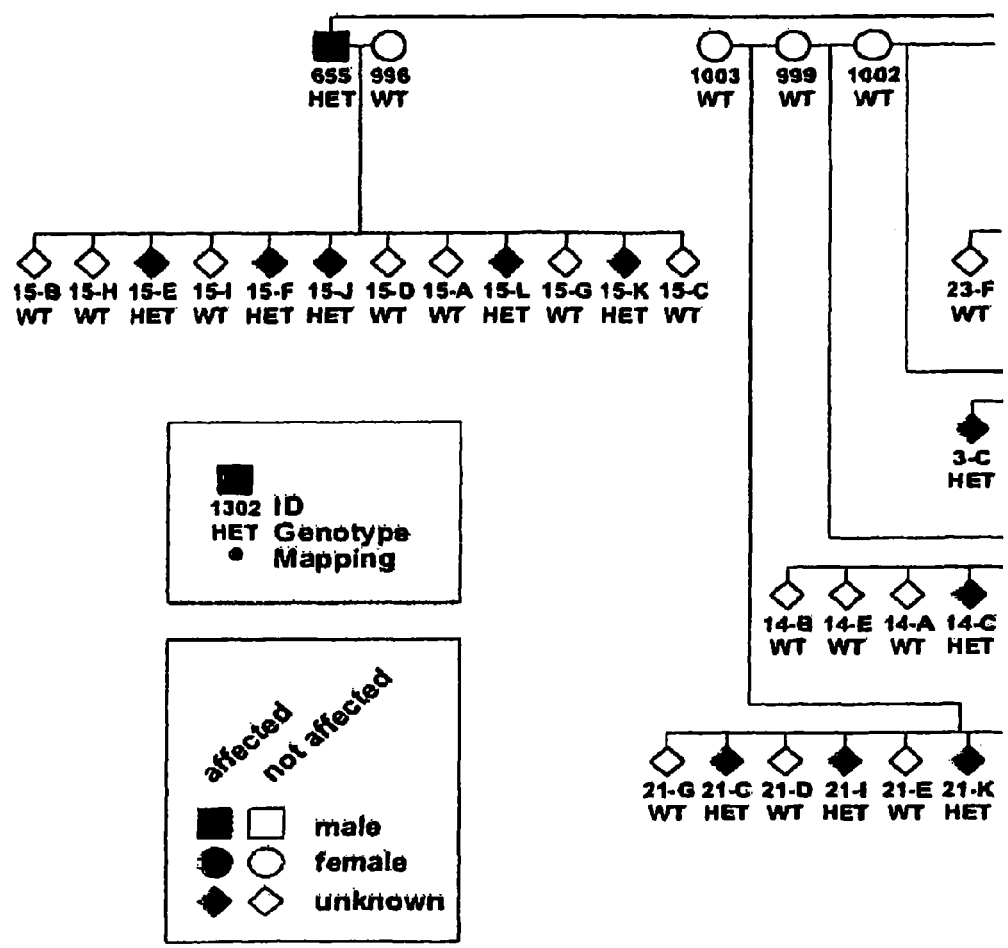
Figure 6B:
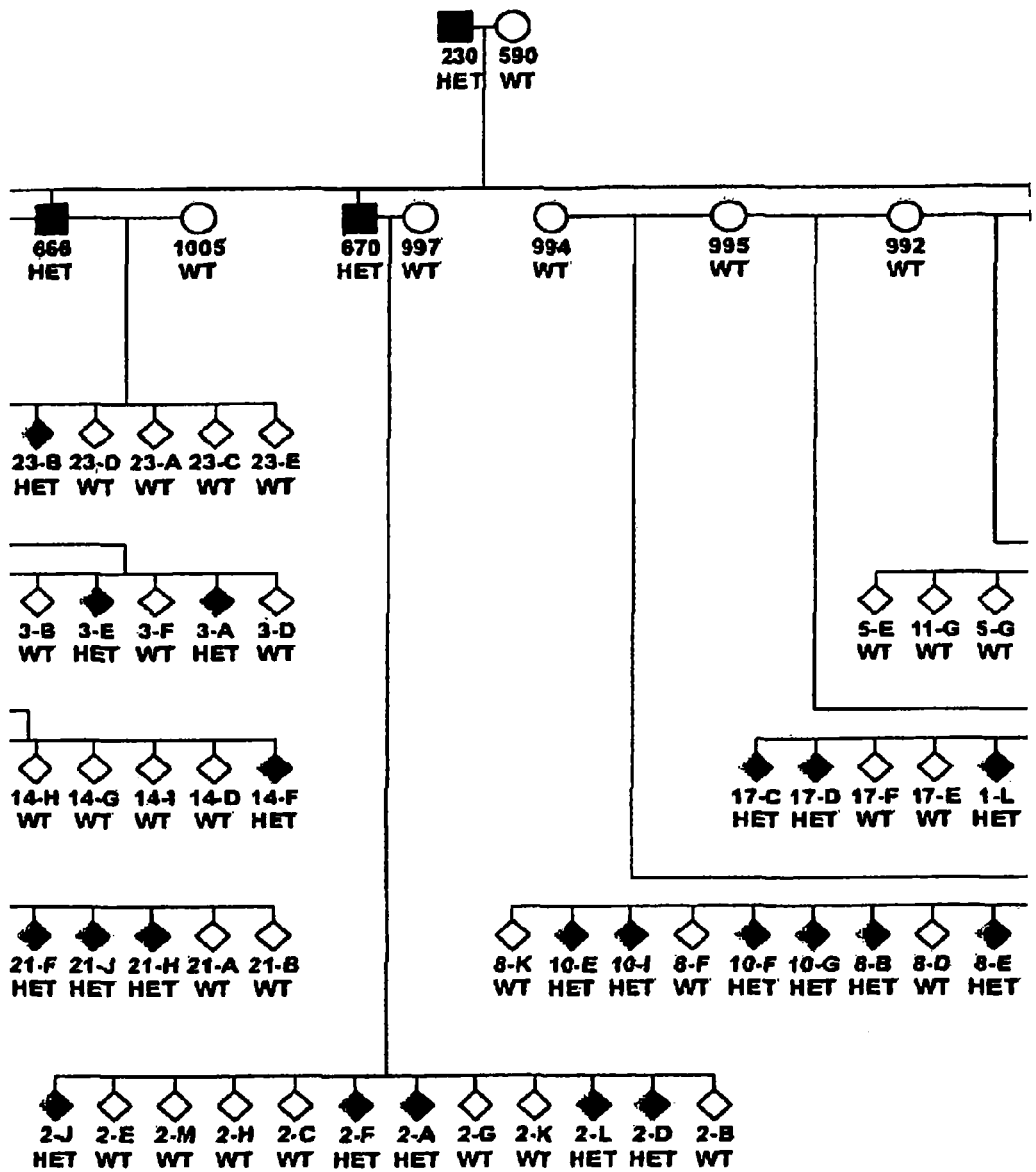
Figure 6C:
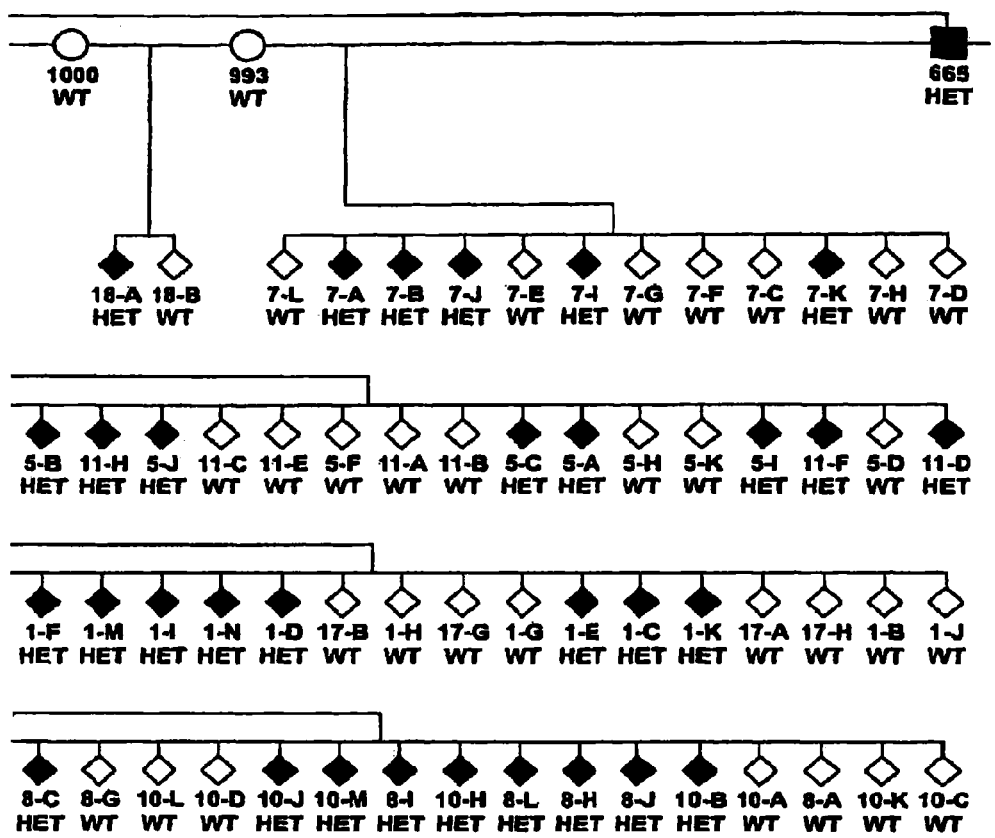
Figure 6D:
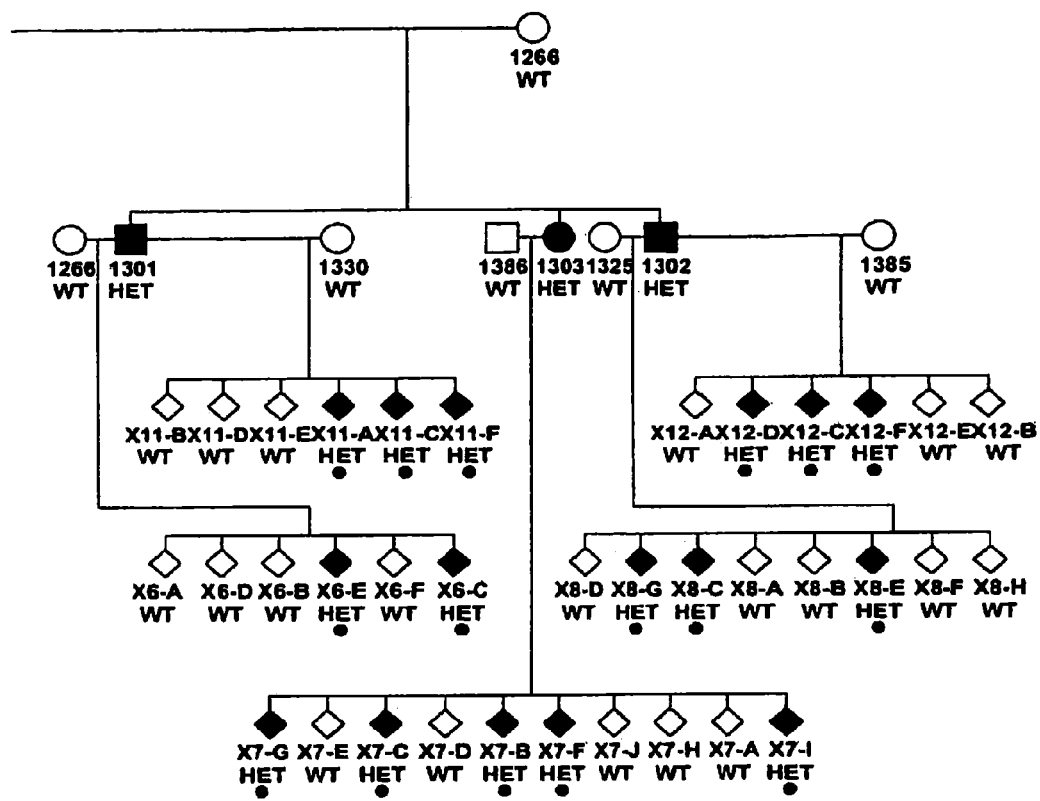

Genetic mapping of a backcross between rats deficient in titin splicing (titin$^{mut}$) and the Brown Norway (BN) reference identified a ~2 Mbp interval on Chromosome 1q55 (FIG. 1a and FIG. 5). Sequence analysis of the coding region of all 8 genes located in this region showed that only RBM20 differed between unaffected and affected rats with a 95 kbp deletion that removes exon 2-14 encoding the RNA binding motive- and the $Zn^{2+}$ finger domains. The deletion was confirmed by Southern blot and quantitative RT-PCR in hetero- and homozygous Rbm20 deficient rats (FIG. 1b, c). In addition, all 191 animals from two independent backcrosses that showed complete co-segregation between the titin splice defect and the RBM20 mutation were genotyped (FIG. 6). Finally, an antisense approach was used in cultured HL-1 murine cardiomyocytes to reproduce the effect of reduced RBM20 expression on titin splicing (FIG. 1d).

Heterozygous and homozygous RBM20 null alleles resulted in left ventricular dilatation as determined by echocardiography in age matched male adult animals. While left ventricular diameter in diastole (LVDd) was significantly increased, there were no changes in systolic ventricular dimensions or crude indices of contractility including fractional shortening. Unexpectedly, sudden death was found from 11 months onwards in both heterozygote and homozygote RBM20 deficient animals, accompanied by increased interstitial and subendocardial fibrosis (FIG. 2c-f). It is remarkable that although Rmb20 deficiency has a profound effect on the mature titin protein, none of the previously described titin deficient animal models or titin mutations in human cardiomyopathy reported to date exhibit a similar pathology[6-9]. This suggests that additional substrates for RBM20 may result in this phenotypic progression.

Figure 7C:
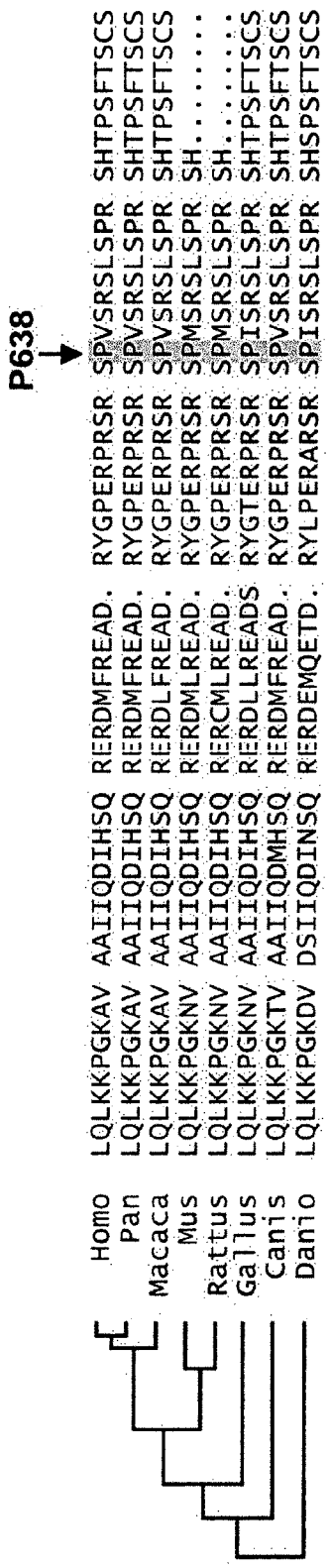

A screen for RBM20 mutations in human families with autosomal dominant dilated cardiomyopathy (DCM) and sudden cardiac death that map to a syntenic locus on human chromosome 10q25[10] was performed. These analyses identified a heterozygous missense mutation in exon 9 of RBM20 (P638L) that completely co-segregated in this family (FIG. 7a). The variant was not reported in dbSNP or present in 812 control chromosomes. An independent cardiomyopathy family (DCM100) that maps to 10q25 does not display arrhythmia or sudden death[10] and the inventors excluded mutations of RBM20 as the underlying defect by sequence analysis of the complete RMB20 coding region in two index patients and found normal RBM20 mRNA levels and titin isoform expression in the left ventricle of a third transplanted patient (data not shown). These results show that 10q22-26 is a DCM-hotspot with 5 independent loci associated with the disease[10].

Figures 7D, 7E:
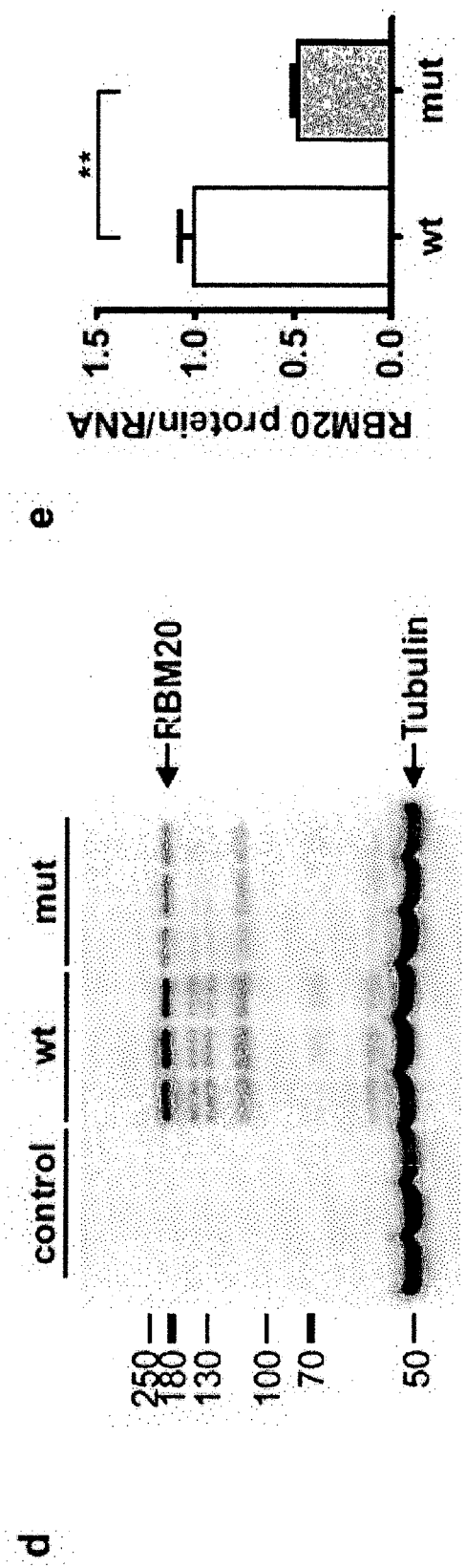

The human RBM20 mutation that was identified was outside the RNA-binding and Zinc-Finger domains, but it is evolutionary well conserved (FIG. 7). Not only have proline to leucine mutations in Prion Protein (P120L) and Seqestosome (P392L) been linked to inherited disease[11,12], but the Pro-to-Leu exchanges in thymidilate synthase and Guanylate cyclase activating protein-1 have been shown to increase susceptibility to protein degradation[13,14]. It is tempting to speculate that the mutation in the DCM50 family causes a similar effect resulting in reduced RBM20 protein levels.

Figure 3A:
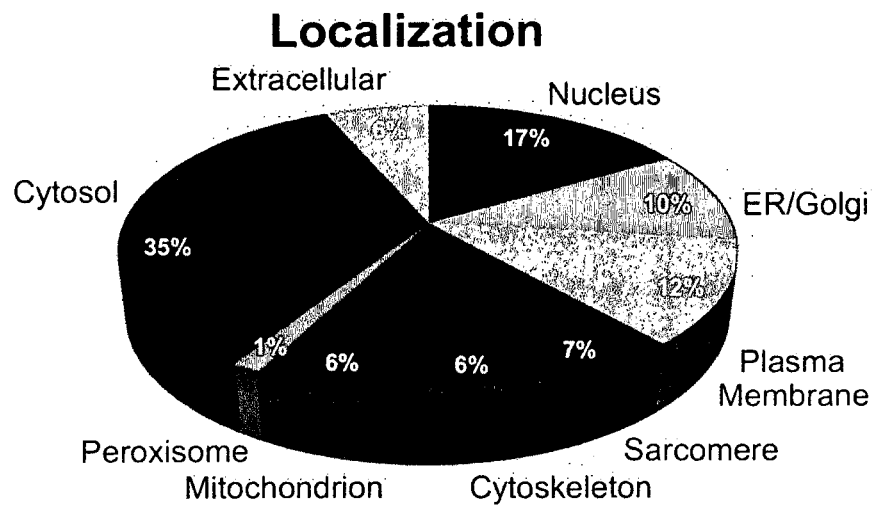
Figure 3B:
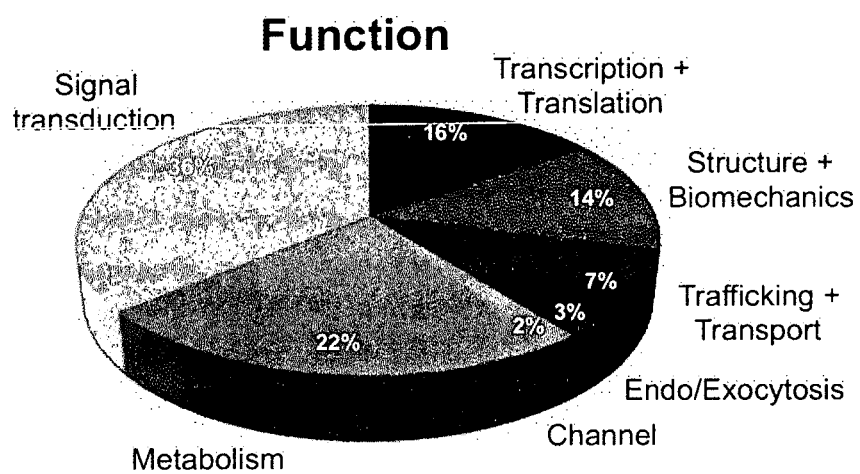
Figure 9:
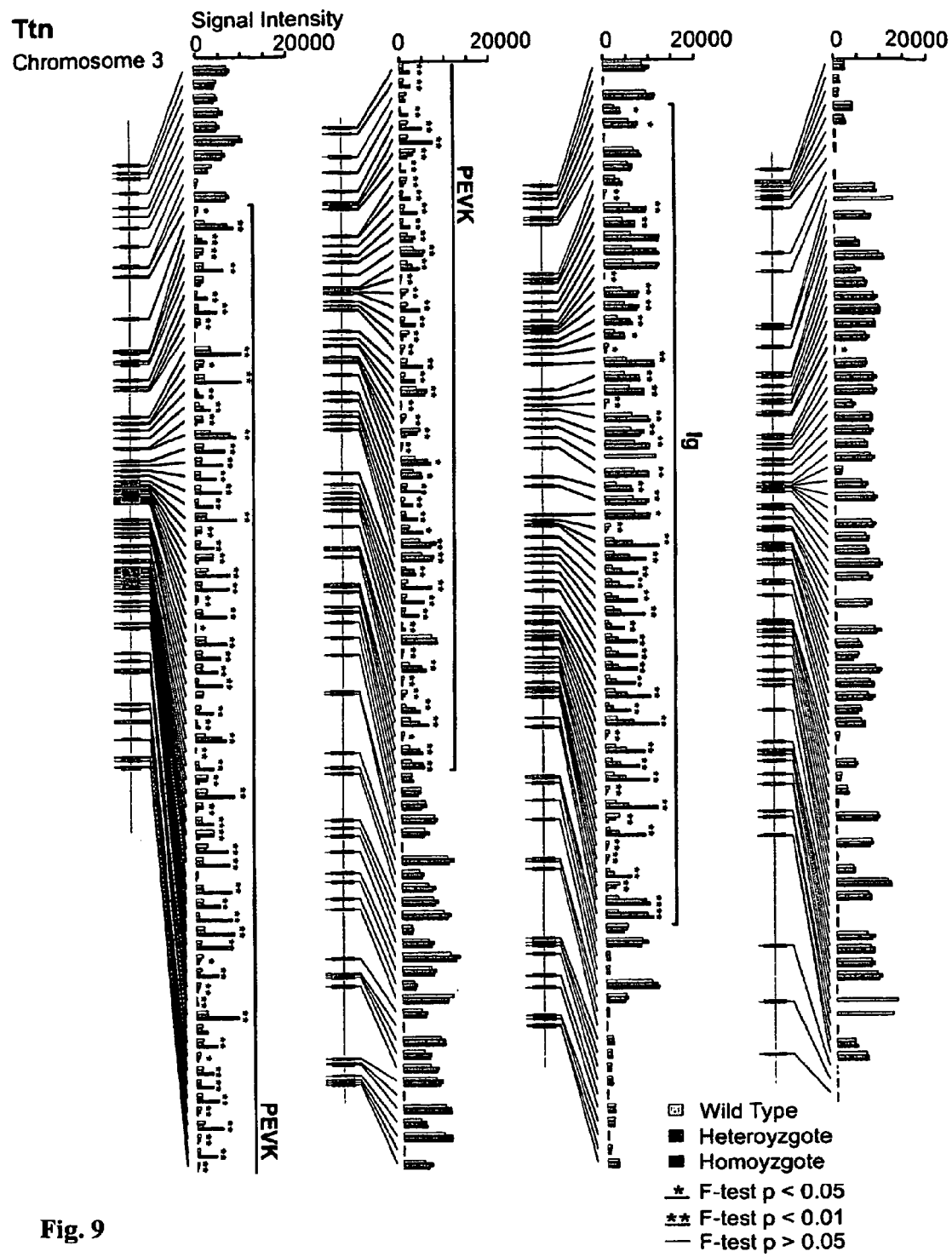

To elucidate the pathophysiology and determine if the additional genes related to cardiac function are perturbed, genome-wide exon based expression profiling was used to investigate RBM20 dependent alternative splicing (FIG. 2). Titin was confirmed as the most extensively misspliced gene with 54 exons affected (FIG. 3 and FIG. 9). Loss of RBM20 perturbed the splicing of a total of 67 transcripts (genome wide corrected FDR <5%), representing genes with diverse functions ranging from signal transduction and metabolism to biomechanics and ion-transport (FIG. 3a,b). For the majority of 37 genes RBM20 affected the splicing of only a single exon; in the remaining 30 genes multiple exons were affected. In addition to titin, which has previously been linked to DCM[7] other known disease genes where splicing was disrupted included the ion-channel KCNQ1 involved in cardiac arrhythmia and sudden death[15] (FIG. 10), as well as multiple genes that encode cardiomyocyte structural proteins.

Figure 4A:
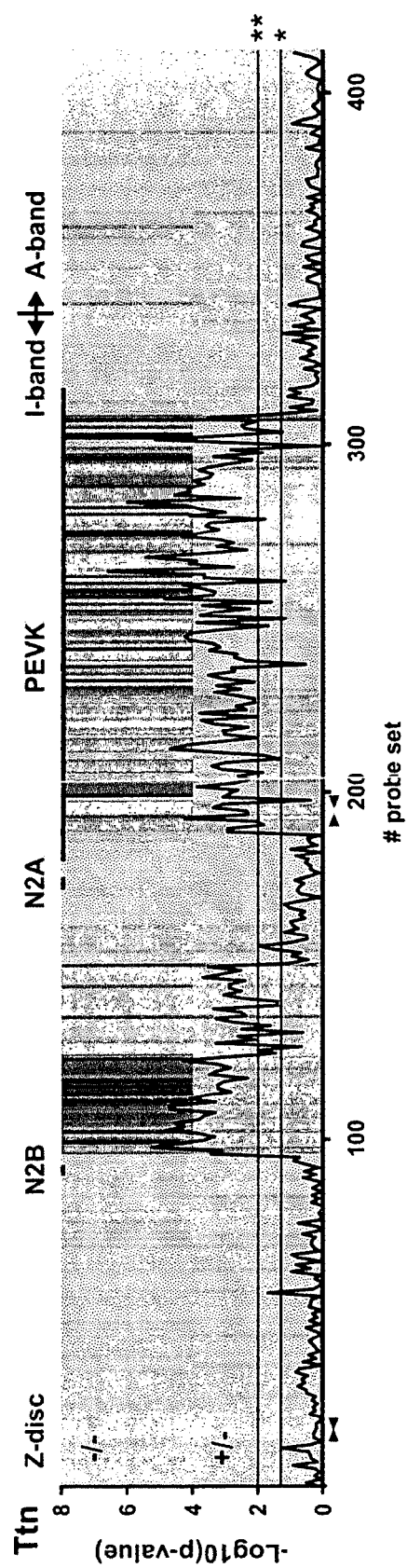
Figure 4B:
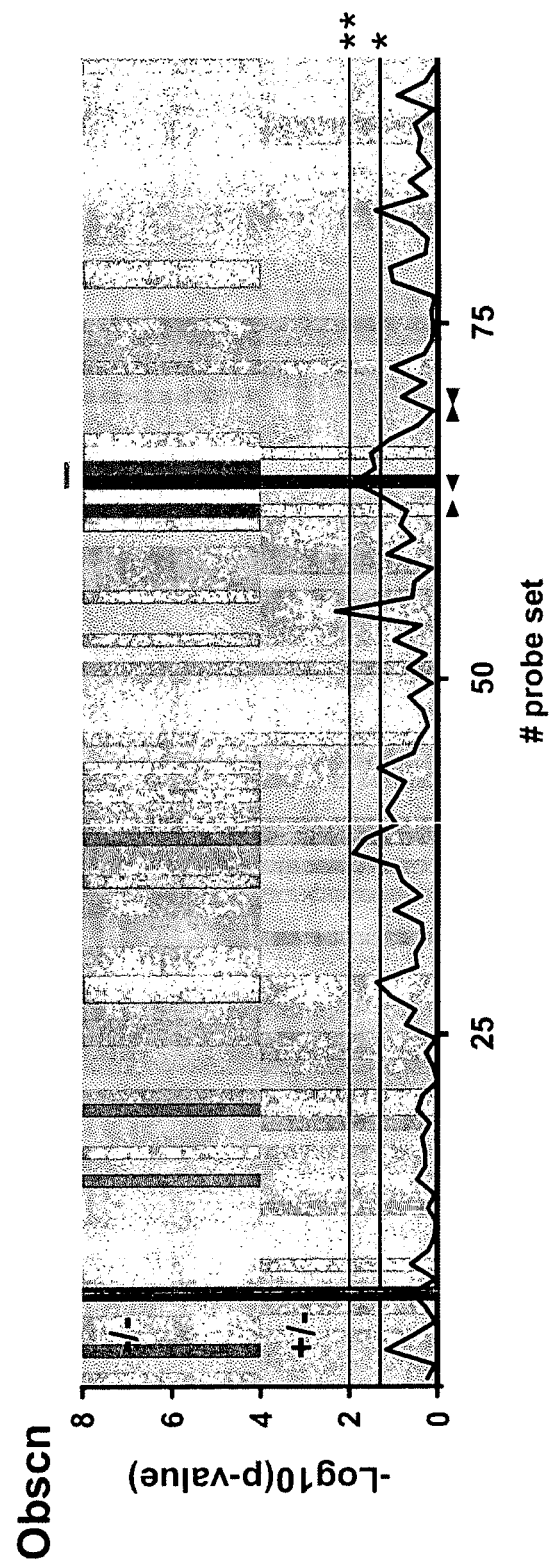
Figure 4C:
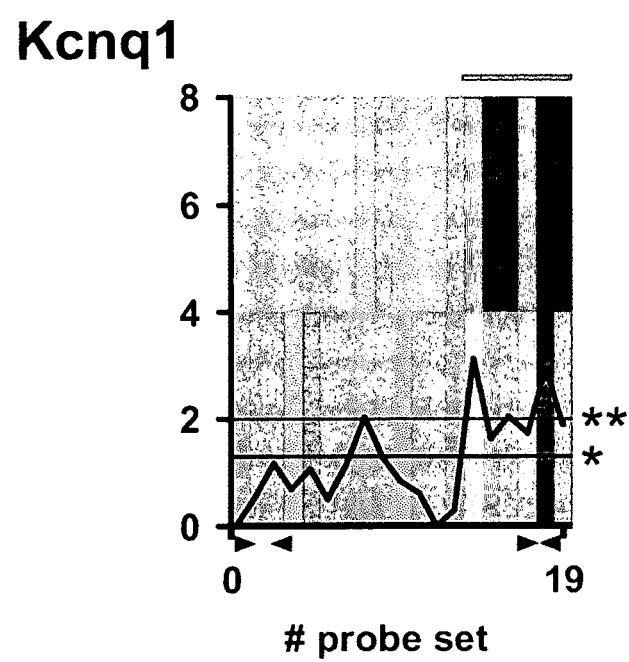
Figure 4D:
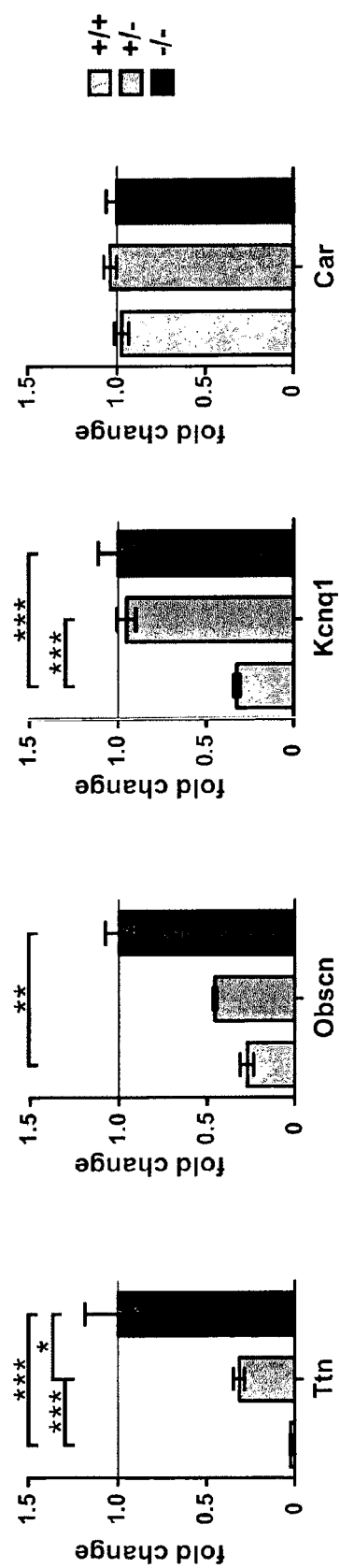
Figure 10:
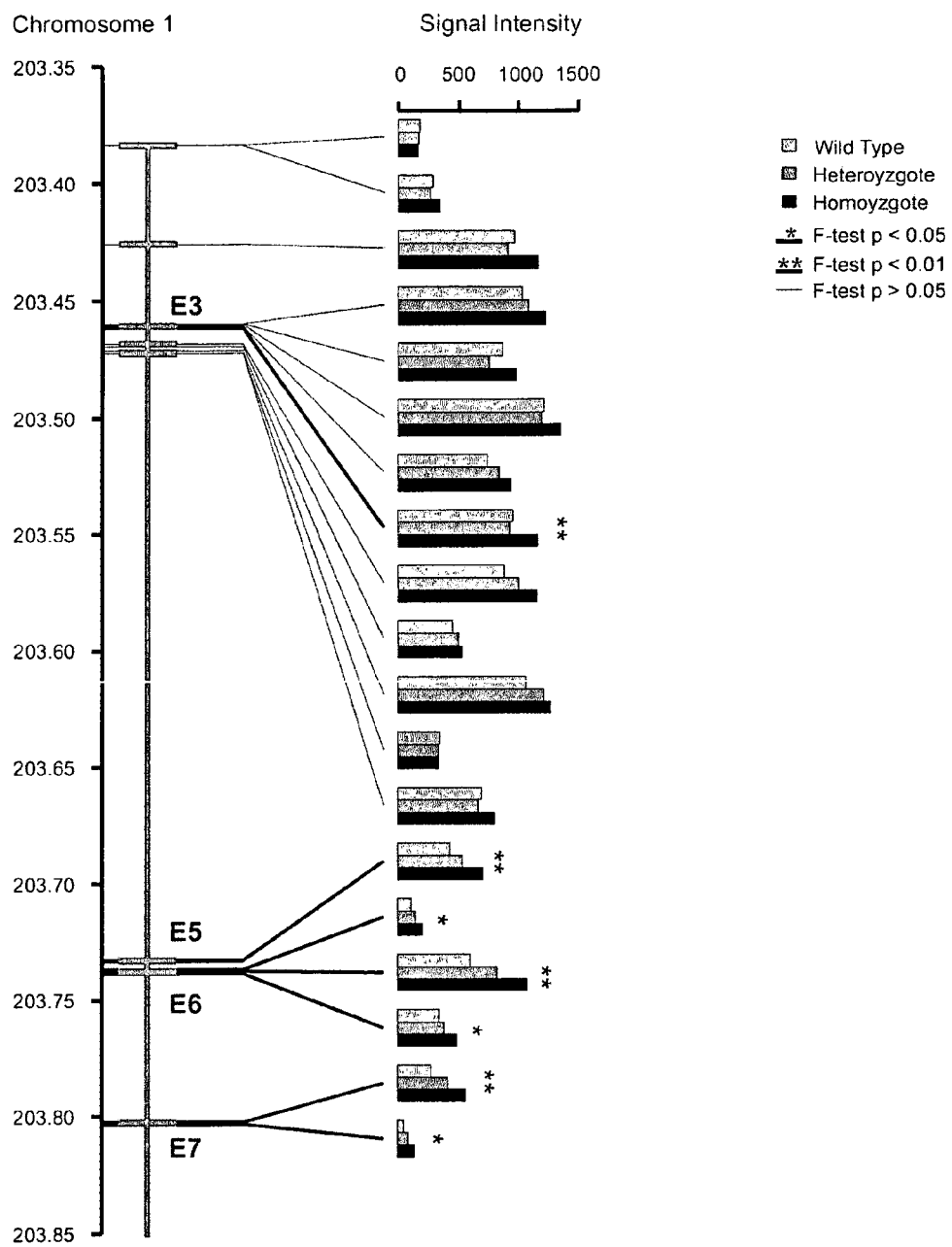
Figure 11A:
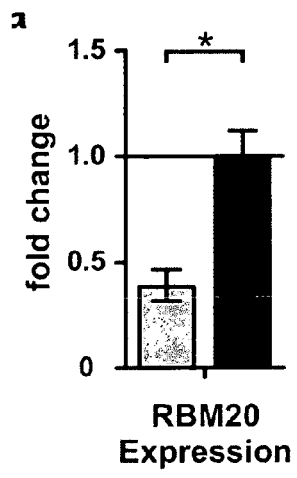
Figure 11B:
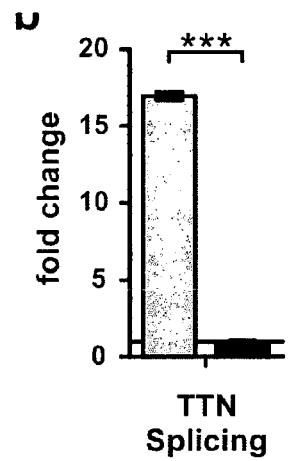
Figure 11C:
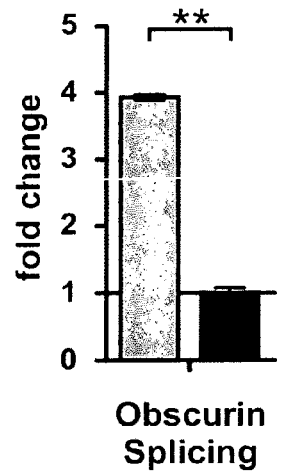
Figure 11D:
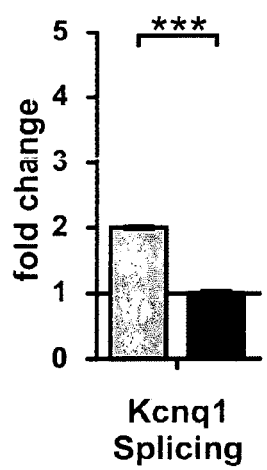
Figure 11E:
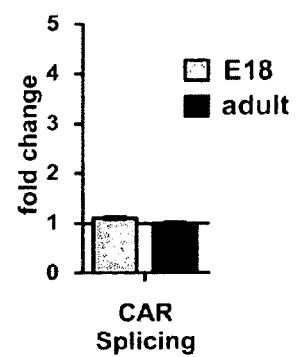

Using a simple heat-map, the splicing effects of RBM20 for genes with a previously published association to cardiomyopathy and sudden death, the inventors visualized in which at least two exons were involved. This enabled us to define the gene dosage effect of RBM20 on alternative splicing of its target genes at the level of the individual exon (FIG. 4). Reduced RBM20 expression in heterozygotes caused an intermediate phenotype while the loss of RBM20 prevented alternative splicing (light blue vs. dark blue for exons that were no longer spliced out/light red vs. dark red for newly included exons). For titin, 42 exons were found that were upregulated and 12 that were downregulated in response to the loss of RBM20—consistent with the expression of larger titin isoforms (FIG. 4a). These alternatively spliced exons were restricted to the elastic PEVK- and the immunoglobulin-rich region within the I-band and helped explain the increased passive elasticity of RBM20 deficient sarcomeres[3]. Obscurin isoform expression showed the inclusion of two exons (blue) that encode a putative kinase domain. Aberrant splicing of KCNQ1 resulted in a truncated isoform lacking the 3'exons E5-E7 that encode the tetramerization domain required for normal channel assembly[16] (FIG. 4, FIG. 10). Potential roles for this truncated protein in cardiac physiology are currently unknown. The exon array data were verified independently by qRT-PCR with the expected upregulation of the alternatively spliced exons in titin, obscurin, and Kcnq1 in response to graded loss of RBM20 (FIG. 4d). Future analysis will have to address how the alternative splicing of diverse functional domains related to biomechanics (titin), signal transduction (obscurin), and ion transport coordinately adapt cardiac function in developmental change and disease.

The role of RBM 20 in the physiologic perinatal isoform transition and in human dilated cardiomyopathy was revisited. Using RTPCR-based analysis of RBM20 dependent alternative splicing in embryonic and adult hearts from wild-type rats, the inventors confirmed the predicted effects on splicing not only of titin, but also of obscurin and Kcnq1, associated with increased postnatal expression of RBM20 (Figure S7). These data confirm that regulation of titin's mechanical properties both by posttranslational modification (phosphorylation of the N2B region by PKA in response to adrenergic regulation[4]) and by alternative splicing (skipping of exons in the tandem Ig- and PEVK region by RBM20) is tightly integrated by a master regulator to provide a coordinated cellular response to environmental cues. In response to adrenergic stimulation this regulator is PKA that not only increases contractile force by phosphorylation of Troponin I and enhances $Ca^{2+}$ reuptake via phospholamban[17]—but also reduces passive tension by phosphorylating titin. Our extended splice-analysis suggests that RBM20 plays a parallel role in postnatal development with the indication of a concerted action on biomechanics (titin), electrical activity (Kcnq1), and structure/signal transduction (obscurin).

Dilated cardiomyopathy (DCM) is a leading cause of heart failure and cardiac transplantation in Western countries and has been extensively studied[18]. While there is evidence of a substantial inherited contribution to DCM, there is also significant pleiotropy and reduced penetrance within families[19]. Numerous loci have been identified, and though the causal genes are known at only a small subset of these, they include genes encoding sarcomeric contractile proteins, cytoskeletal proteins, nuclear membrane proteins, and the dystrophin associated glycoprotein complex[20]. The discovery of RBM20 as a novel trans regulator of these, and many other, genes not only defines a novel class of cardiomyopathies, but also suggests a potential unifying factor in the pathophysiology of human heart failure. Notably, while >20% of human genetic diseases have been attributed to mutations in cis acting splice-elements, to date only four trans effects have been described[21,22]. Understanding the role of RBM20 in the coordinated regulation of myocardial and vascular genes during development and disease will help elucidate the mechanisms of human heart failure, and potentially lead to novel diagnostic and therapeutic tools.

Materials and Methods

Experimental crosses, genotyping, and genetic mapping. For mapping of the titin splice deficient mutation two independent backcrosses were established. Genetic mapping was carried out using a total of 4391 informative SNPs. The inventors then tested for a shared SD/F allele between all 16 affected animals genotyped from the N1 (SD/F×BN) backcross across all informative SNPs. The probability of a given allele distribution was calculated using the one-sided binomial test under the null hypothesis of a random selection of the backcross individuals. Correction for genome wide multiple testing correction was performed using the Benjamini Hochberg procedure[23].

Tissue culture. HL-1 cells (murine atrial myocytes) were transfected with Lipofectamine 2000 and 50 nM siRNA using 2 primer pairs specific for RBM20 (SI1-3) and one scrambled primer pair (NS). Cells were harvested at 48 h after transfection for protein analysis.

Cardiac phenotyping. Cardiac dimensions and function were evaluated by echocardiography of sedated rats (IP administration of 25-50 mg/kg ketamine) using a Sonos 5500 ultrasonograph with a 15-MHz transducer (Philips, Andover Mass.) following the guidelines of the American Society of Echocardiography guidelines. To detect fibrosis hearts from 9 to 18 month old rats were fixed in 4% paraformaldehyde and paraffin-embedded, and sections midway between base and apex were stained with Massons trichrome.

Exon profiling. RNA from the left ventricle was used in the Affymetrix GeneChip Whole transcript (WT) Sense Target Assay to generate amplified and biotinylated sense-strand DNA targets from the entire expressed genome. Hybridization was performed using the GeneChip ST Exon arrays (Affymetrix). 204868 probes of the nine Arrays were RMA normalized using the Partek Genomic Suite version 6.3 beta and after removal of probes with a maximum expression level <64 (n=84126) two way ANOVA calculation were performed.

Animal procedures. The rat strain with altered splicing has been previously described[3,24]. Splice deficient and control animals were sacrificed to harvest tissues for RNA-expression analysis (E18, P1, P20, P49, >P100) and the documentation of altered titin isoform expression (F2: P1-5, adults: 6 m-12 m). Liver samples were used to obtain DNA for genotyping by PCR and southern blot. RNA was extracted from left ventricles for expression analysis. Cardiac dimensions and function were evaluated by echocardiography of sedated rats (IP administration of 25-50 mg/kg ketamine) using a Sonos 5500 ultrasonograph with a 15-MHz transducer (Philips, Andover Mass.). For functional calculations the inventors followed American Society of Echocardiography guidelines. In the LV parasternal long axis 4-chamber view the inventors derived fractional shortening (% FS) and ventricular dimensions. All experiments involving animals were carried out following institutional and NIH guidelines, "Using Animals in Intramural Research".

Histopathology. Hearts were removed from 9 to 18 month old rats, fixed in 4% paraformaldehyde, and paraffin-embedded. Sections midway between base and apex were stained with Massons trichrome. Relative areas of connective tissue and cardiomyocytes were determined independently as outlined herein.

Tissue culture. HL-1 cells (murine atrial myocytes) were transfected with Lipofectamine 2000 (4 μl) and 50 nM siRNA using 3 primer pairs specific for RBM20 (SI1-3) and one scrambled primer pair (NS). Cells were harvested at 48 h after transfection for protein analysis.

Experimental crosses, genotyping, and genetic mapping. Affected animals with the titin splice defect were kept in the colonies of the University of Madison on a mixed SD/F344 (SD/F) background. For mapping these animals were crossed with either F344 or BN rats to establish two independent F1 populations. Each F1 cross was then backcrossed to establish 2 independent N1 crosses. SNP genotyping was performed on genomic DNA using a 10K SNP assay as previously reported[25] using 23 DNA samples including three F1 (SD/F× BN), four BN, and 16 affected splice deficient rats from the SD/F×BN backcross[26,27]. The final dataset included a total of 4391 informative SNPs that covered the autosomal genome with an average distance of 568 kb. The inventors then tested for a shared SD/F allele between all 16 affected animals genotyped from the N1(SD/F×BN) backcross across all informative SNPs. The probability of a given allele distribution was calculated using the one-sided binomial test under the null hypothesis of a random selection of the backcross individuals. Correction for genome wide multiple testing correction was performed using the Benjamini Hochberg procedure[23]. Mapping results were confirmed by resequencing SNPs within the candidate interval.

Expression analysis of the mutant Rbm20. HEK 293 cells were transfected with 9 μg of mammalian expression vector containing either WT Rbm20-myc-His or P641L Rbm20-myc-His using Turbofect transfection reagent (Fermentas). Cells were harvested 48 h after transfection and split for parallel analysis for qRT-PCR and Western Blot analysis. Cell pellets for protein analysis were lysed in mild RIPA buffer (w/o SDS) supplemented with Complete, EDTA-free Protease inhibitor Cocktail (Roche) using TissueLyser II (QIAGEN) and ¼" ceramic spheres (MP Biomedicals) for 2 min at 25 Hz. Protein levels were evaluated by probing against myc-tag using monoclonal Mouse α-c-myc (9E10) (Invitrogen) following standard Western Blot procedure.

RNA was extracted by using RNeasy Mini Kit (QIAGEN). RT-PCR was carried out by using ThermoScript™ RT-PCR System (Invitrogen) followed by SYBR-Green RT-PCR using the forward primer (5'-cag get tgc caa gaa aac tc-3') and the reverse primer (5'-g ctc gga tcc act agt cca g-3'), specific for exogenous Rbm20 and the 18S amplicon (forward: 5'-gtc ccc caa ctt ctt aga g-3' and reverse: 5'-cac cta cgg aaa cct tgt tac-3') for normalization. RNA levels were evaluated using iQ SYBR Green Supermix (BioRad) on a StepOnePlus RT-PCR system (Applied Biosystems).

Exon profiling. RNA from the left ventricle was used in the Affymetrix GeneChip Whole transcript (WT) Sense Target Assay to generate amplified and biotinylated sense-strand DNA targets from the entire expressed genome. Hybridization was performed using the GeneChip ST Exon arrays (Affymetrix).

204868 probes of the nine Arrays were RMA normalized using the Partek Genomic Suite version 6.3 beta and after removal of probes with a maximum expression level <64 (n=84126) two way ANOVA calculation were performed. Additional detail is provided elsewhere herein.

Agarose gel-electrophoresis. Protein samples from left ventricles or cultured cells were homogenized in sample buffer (8 M urea/2 M thiurea/0.05 M Tris pH 6.8/75 mM DTT/, 3% SDS0.05% bromophenol blue) and titin isoforms were separated using an SDS/agarose gel electrophoresis system as described previously[28].

Mutation screening in the human population. Genomic DNA was isolated from venous blood samples and 14 RBM20 exons were PCR amplified according to standard protocols (Taq PCR Core Kit, QIAGEN, Hilden, Germany) using oligonucleotides designed for the amplification of coding sequences including 60-100 bp of flanking intronic sequences. Sense and antisense strands were directly sequenced sequenced using fluorescent dye terminator chemistry on ABI 3730 instruments. Both strands of the amplicons were sequenced to obtain unambiguous sequence reads. >99% of sequencing reads passed quality filters and had unambiguous sequence results. Sequence reads were processed and assembled using Phred and Phrap, and analysed using Polyphred and Consed (http://www.phrap.org/; http://droog.mbt.washington.edu/PolyPhred.html). Mutation screening of all exons of RBM20 was carried out with genomic DNA samples from 2 affected and 2 unaffected family members of CM-50, CM-100, and in 70 unrelated index cases with idiopathic DCM. Primers were designed in intronic sequences flanking all 14 exons based on reference mRNA sequence (NCBI accession number EU822950.1). Segregation of the P638G mutation with the disease phenotype in the CM-50 pedigree was tested in all available family members. Amino acid changes due to mutations are annotated according to NCBI accession number ACF49364.1. 406 healthy individuals of Western European descent including 250 people from Scotland served as controls for the presence of the RBM20 mutation observed in the CM-50 family and the sporadic patient. The 250 Scottish controls were taken from the "Genetic mechanisms of cardiovascular disease cohort" at the University of Glasgow. s159852, sense 5'-GC-CUUUGGAUCUCGACUUAtt-3' SEQ ID NO. 7, antisense 5'-UAAGUCGAGUACCAAAGGCag-3' SEQ ID NO. 8; or s159853, Sense 5'-CGUUCUCGAAGUCCAAUGAtt-3' SEQ ID NO. 9, antisense 5'-UCAUUGGACUUC-GAGAACGtg-3'SEQ ID NO. 10.

Tissue culture procedures. HL-1 cells[29] were grown in 24 well plates (40,000 cells per well) on Claycomb media (JRH Biosciences) supplemented with 1% penicillin/streptomycin, 1% 10 mM norepinephrine, 1% 200 mM L-glutamine, and 10% fetal bovine serum (Sigma-Aldrich). Transfection and siRNA concentration (Ambion) were optimized with GAPDH (50 nM Cy3-labeled). A combination of Lipofectamine 2000 (4 μl) and 50 nmol/l siRNA (s159851, sense 5'-CCAUCGAAAAGAGACUAAAtt-3' SEQ ID NO. 11, antisense 5'-UUUAGUCUCUUUCGAUGGta-3'SEQ ID NO. 12; s159852, sense 5'-GCCUUUGGAUCUCGACU-UAtt-3' SEQ ID NO. 7, antisense 5'-UAAGUCGAGUAC-CAAAGGCag-3' SEQ ID NO. 8; s159853, Sense 5'-CGUU-CUCGAAGUCCAAUGAtt-3' SEQ ID NO. 9, antisense 5'-UCAUUGGACUUCGAGAACGtg-3'SEQ ID NO. 10) (Ambion) designed for inhibition of Rbm20 (human, rat, and mouse) was found to give best results. A control included Lipofectamine without siRNA and one scrambled siRNA based on the nucleotide sequence of s159851 (sense 5'-CCUACGUUGGAAGCGAUUAtt-3' SEQ ID NO. 13, antisense 5'-UAAUCGCUUCCAACGUAGGta-3' SEQ ID NO. 14), which lacked homology to any other gene by BLAST search. Cells were harvested at 48 h after transfection for analysis of protein changes.

Annotation of RBM20. Full length rat Rbm20 (6682 bp) was cloned, sequenced, and annotated. It contains 102 bps of 5' UTR and 2956 bp of 3' UTR. The revised coding region is 3624 bp (up from 1791 bp in current GenBank NM_001107611.1). Rbm20 contains a single RNA-recognition motif (RRM) spanning amino acid positions 522-592 and also contains a single U1-like zinc finger motif (1136-1174). The revised sequence data has been deposited in the NCBI database (Accession number EU562301). The rat and human amino acid sequences are 76% identical with greatest similarities in the RRM and zinc finger regions.

Genotyping by PCR and Southern blot. For genotyping, template DNA was prepared from rat liver as published previously[30]. For Southern blot analysis, genomic DNA was digested with Hind III overnight and probed with a PCR product generated with primers Exon 2 forward (5'-CCAGCTCACCCTCCATCG-3') and Exon 2 reverse (5'-GC-CATAGTCATAGAACCCTG-3') following standard procedures[30]. The deletion was confirmed by PCR (primers P1, 5'-GTCTTCATGATCCTGGAGTG-3; and P2, 5'-GGT-GTGGGGTTATGGAGTC-3') (compare FIG. 1A). Genotyping of pedigree animals was conducted by PCR multiplexing with two pairs of primers [WT forward (5'-GAAGTCCAAT-GAGCCGATC-3') and WT reverse (5'-CTCCTTCTTG-GTCTCTGTC-3') for wild type, product size 432 bp/M forward (5'-GTCTTCATGATCCTGGAGTG-3') and M reverse (5'-GGTGTGGGGTTATGGAGTC-3') for homozygous mutant, product size 868 bp] (FIG. 6).

Echocardiography (rat). Transthoracic echocardiography was performed using a Sonos 5500 ultrasonograph with a 15-MHz transducer (Philips, Andover Mass.). For acquisition of two-dimensional guided M-mode images at the tips of papillary muscles and Doppler studies, rats were sedated by IP administration of 25-50 mg/kg ketamine and maintained on a heated platform in a left lateral decubitus or supine position. The chest was shaved and prewarmed coupling gel applied. Mitral and aortic flows were measured using Doppler pulse wave imaging. End diastolic and systolic left ventricular (LV) diameters as well as anterior and posterior wall (AW and PW respectively) thicknesses were measured on line from M-mode images using the leading edge-to-leading edge convention. All parameters were measured over at least three consecutive cardiac cycles and averaged. Left ventricular fractional shortening was calculated as [(LV diastolic diameter−LV systolic diameter)/LV diastolic diameter]×100 and LV mass was calculated by using the formula [1.05 ×((diastolic posterior wall+diastolic anterior wall+LV diastolic diameter)3−(LV diastolic diameter)3)]. Relative wall thickness was calculated as 2*diastolic posterior wall/LV diastolic diameter. Heart rate was determined from at least three consecutive intervals from the pulse wave Doppler tracings of the LV outflow tract. Isovolumetric relaxation time was measured as the time from the closing of the aortic value to the opening of the mitral value from pulse wave Doppler tracings of the LV outflow tract and mitral inflow region. The same person obtained all images and measures.

Histopathology. Hearts were removed from 9 to 18 month old rats and fixed in 4% formaldehyde buffered with PBS. Following dehydration and paraffin embedding, cross sections midway between the base and the apex were cut, deparaffinized, and stained with Massons trichrome. Images were collected using a Zeiss Axiovert 200 microscope with an AxioCAM HR digital camera and 5× or 20× objectives. Relative area fractions were estimated using the segmentation tool of IPLabs 3.6 (Signal Analytics). With the trichrome stain, the percent areas of blue (connective tissue), red (cardiomyocytes), and white (tissue holes) were determined independently. A data set was included in the analysis if the sum of these three measures was in the range from 90-110%. The percent fibrosis was estimated by comparing the blue-green area to the sum of the blue-green and red areas. Four to eight separate images from the interstitial regions were processed for each slide.

Exon profiling. For RNA preparation from the left ventricle, the inventors used a trizol base method. Briefly, the tissue was homogenized with a homogenizer in the presence of trizol (Invitrogen), extracted with chloroform, precipitated in ethanol, and dissolved in nuclease-free water. After quality control (2100 Bioanalyzer, Agilent) and DNAse digestion, RNA was purified using Rneasy columns (Qiagen) and stored at −80 ° C. To reduce ribosomal RNA (rRNA) the inventors used the RiboMinus Kit from Invitrogen (Carlsbad, Calif.).

Exon profiling was performed using the Affymetrix GeneChip Whole transcript (WT) Sense Target Assay to generate ampflified and biotinylated sense-strand DNA targets from the entire expressed genome. Starting with 1μg RNA, double-stranded cDNA was synthesized with random hexamers coupled to a T7 promoter sequence. This cDNA was transcribed into cRNA molecules that were subsequently converted into single-stranded DNA in the same orientation as original mRNAs by random primed reverse transcription with random hexamers. Hybridization was performed using the GeneChip ST Exon arrays (Affymetrix). 5 μg cDNA were fragmented and labeled for hybridization.

Figure 8:
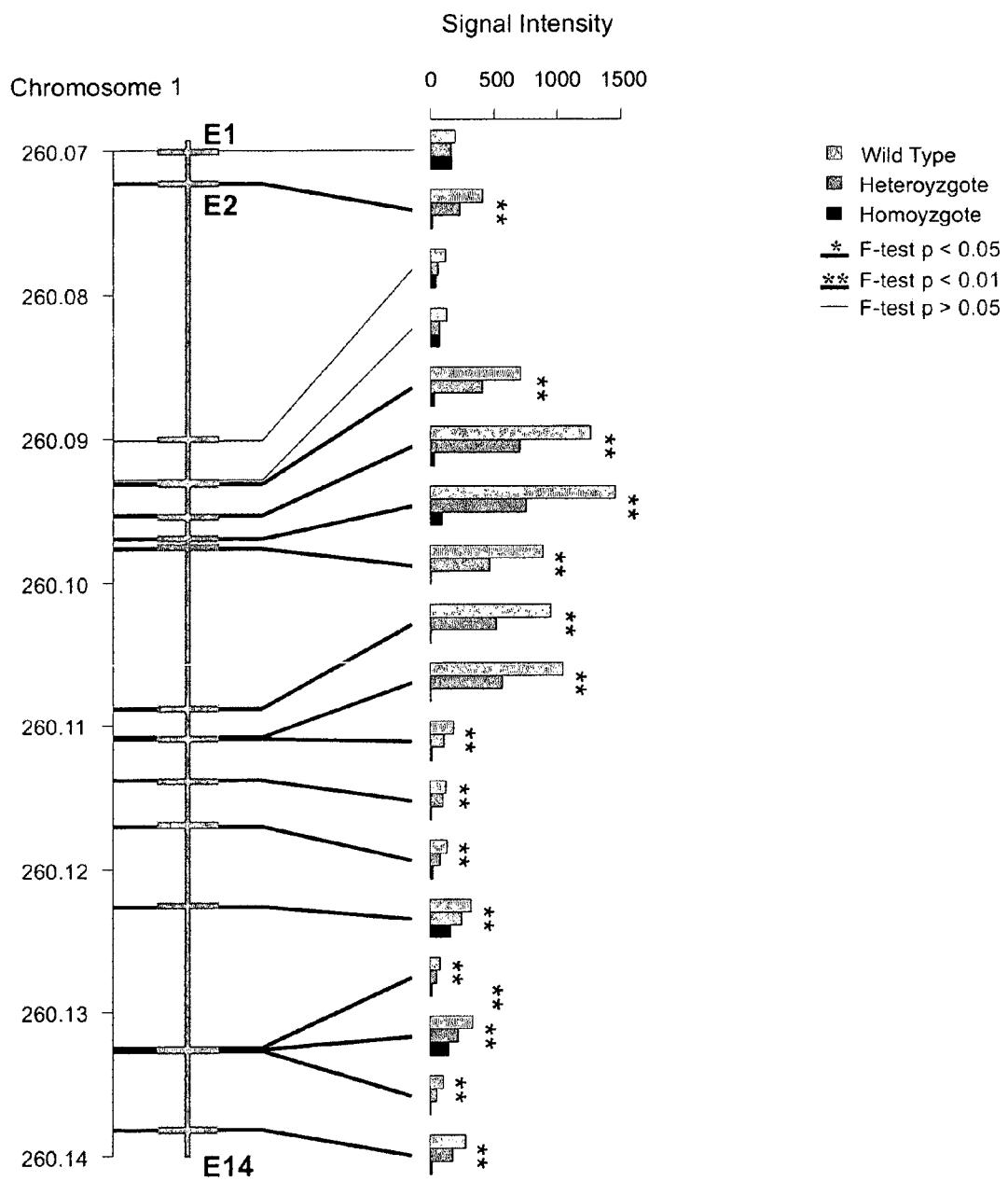

Preprocessing and analysis of exon data. Arrays were quantile-normalized with respect to the probe GC content as described by Kwan et al.[31] Probes containing known SNPs in different rat populations (n=105,037) were removed to prevent high false positive rates caused by hybridization artifacts[32] using the STAR recourse of 2,976,313 SNPs.[33] Transcripts with low expression levels were removed by the Affymetrix DABG method (p≥0.05) and by a maximum expression cutoff <50. The probe and probe set based data filtering resulted in 365,787 probe sets and 55,878 meta-probe sets defined in the full dataset. Signal values from both sets were base two logarithmized after addition of a stabilization constant[32] (8). The analysis of alternative splicing events was performed using the two way ANOVA approach of the Partek Genomic Suite version 6.4. Only Meta-Probe Sets with three or more probe-sets were included in the analysis. The resulting interaction p-values indicate the probability of splicing events. For multiple testing correction the Bejamini Hochberg procedure was used[34]. Probe sets of genes differentially spliced at FDR <5% were analyzed for differences between the three conditions (wildtype/heterozygote/knockout) using the f-test followed by the LSD post hoc test if a positive f-test results (p<0.05) was present. Differential expression of summarized gene level expression was calculated using the f-test statistic followed by a FDR multiple testing correction. Exons were considered alternatively spliced when the majority of the included probesets were differentially spliced (f-test; p<0.05). $\log_e$ splicing indices were calculated and used for the visualization of splice events as heatmaps. The splicing index was defined as the inter-condition ratio of median probe set signals which has been normalized to the meta-probe set intensity (http://www.affymetrix.com/support/technical/whitepapers/exon_alt_transcript_analysis_whitepaper.pdf). The probe-sets corresponding to RBM20 were used for quality control and produced the expected results with background expression of Exons 2-13 and intermediate expression levels in the heterozygotes (FIG. 8).

Transcript analysis. RNA was prepared from snap frozen tissue using the RNeasy Mini Kit (QIAGEN) followed by cDNA synthesis using Thermoscript First-Strand Synthesis System (Invitrogen). Quantitative real-time RT-PCR (qRT-PCR) was performed in triplicates on an ABI 7900 Real Time PCR Instrument (Applied Biosystems) using the SYBR GREEN PCR Master Mix (Applied Biosystems). Data were analyzed with SDS 2.0 software (Applied Biosystems) and Microsoft Excel, using the AACt method and the expression level of 18S as an internal reference[35]. To confirm alternative splicing by qRT-PCR, the inventors normalized to representative exons within the same gene that were determined as not differentially spliced by exon profiling.

Clinical Evaluation. Patients were recruited at two tertiary referral centers, Massachusetts General Hospital, Boston and the Charité, Humboldt University, Berlin after institutional review board approval. Clinical characteristics of affected family members in pedigrees CM-50 have been reported[36]. In addition, unrelated adult patients fulfilling criteria for dilated cardiomyopathy (DCM) were collected. Cases were considered sporadic when no evidence of familial disease was observed or when no relatives could be clinically evaluated. Patients were classified as familial cases when at least two first-degree relatives were affected.

Probands and available family members were evaluated by history taking, review of medical records, physical examination, 12-lead electrocardiography, 24 h Holter monitoring, and transthoracic echocardiography. Neuromuscular abnormalities were excluded by physical examination. The diagnosis of DCM was made by echocardiography as described previously 36. In brief, DCM was diagnosed if left ventricular enddiastolic dimension was >117% of normal when corrected for body surface area and age and there was evidence of impaired contractility with a left ventricular ejection fraction <50%.

Statistics. For statistical analysis, GraphPad Prism 5.0 software was used. Results are expressed as means±SEM. Statistical significance between groups was determined by T-test or ANOVA followed by Bonferroni's multiple comparison test for hemodynamic data and expression analysis. For survival analysis the inventors used a Log-rank (Mantel-Cox) test and a Log-rank test for trend. The significance level was chosen as P=0.05.

Sequences

SEQ ID NO. 1 Homo sapiens RNA binding motif protein 20 (RBM20), polynucleotide, mRNA, wildtype SEQ ID NO. 2 Rattus norvegicus RNA binding motif protein 20 (predicted) (Rbm20_predicted), polynucleotide, mRNA, wildtype SEQ ID NO. 3 Homo sapiens RNA binding motif protein 20, polypeptide, wildtype SEQ ID NO. 4 Rattus norvegicus RNA binding motif protein 20 (Rbm20), polypeptide, wildtype SEQ ID NO. 5 Homo sapiens RNA binding motif protein 20, polypeptide, with P638L mutation SEQ ID NO. 6 Rattus norvegicus RNA binding motif protein 20, polypeptide, with P641L mutation SEQ ID NO. 7: s159852, sense 5'-GCCUUUGGAUCUC-GACUUAtt-3'

SEQ ID NO. 8: antisense 5'-UAAGUCGAGUACCAAAG-GCag-3'

SEQ ID NO. 9: s159853, Sense 5'-CGUUCUCGAAGUC-CAAUGAtt-3'

SEQ ID NO. 10: antisense 5'-UCAUUGGACUUC-GAGAACGtg-3'

SEQ ID NO. 11: s159851, sense 5'-CCAUCGAAAA-GAGACUAAAtt-3'

SEQ ID NO. 12: antisense 5'-UUUAGUCUCUUUCGAUG-Gta-3'

SEQ ID NO. 13: sense 5'-CCUACGUUGGAAGCGA-UUAtt-3'

SEQ ID NO. 14: antisense 5'-UAAUCGCUUCCA-ACGUAGGta-3'

References

1. Lahmers, S., Wu, Y., Call, D. R., Labeit, S. & Granzier, H. Developmental Control of Titin Isoform Expression and Passive Stiffness in Fetal and Neonatal Myocardium. *Circ Res* (2004).
2. Makarenko, I. et al. Passive stiffness changes caused by upregulation of compliant titin isoforms in human dilated cardiomyopathy hearts. *Circ Res* 95, 708-716 (2004).
3. Greaser, M. L. et al. Mutation that dramatically alters rat titin isoform expression and cardiomyocyte passive tension. *J Mol Cell Cardiol* 44, 983-991 (2008).
4. Yamasaki, R. et al. Protein kinase A phosphorylates titin's cardiac-specific N2B domain and reduces passive tension in rat cardiac myocytes. *Circ Res* 90, 1181-1188 (2002).
5. Cazorla, O. et al. Differential expression of cardiac titin isoforms and modulation of cellular stiffness. *Circ Res* 86, 59-67 (2000).
6. Xu, X. et al. Cardiomyopathy in zebrafish due to mutation in an alternatively spliced exon of titin. *Nat Genet* 30, 205-209 (2002).
7. Gerull, B. et al. Mutations of TTN, encoding the giant muscle filament titin, cause familial dilated cardiomyopathy. *Nat Genet* 30. 201-204 (2002).
8. Peng, J. et al. Cardiac hypertrophy and reduced contractility in hearts deficient in the titin kinase region. *Circulation* 115, 743-751 (2007).
9. Radke, M. H. et al. Targeted deletion of titin N2B region leads to diastolic dysfunction and cardiac atrophy. *Proc Natl Acad Sci USA* 104, 3444-3449 (2007).
10. Ellinor, P. T. et al. A novel locus for dilated cardiomyopathy, diffuse myocardial fibrosis, and sudden death on chromosome 10q25-26. *J Am Coll Cardiol* 48, 106-111 (2006).
11. Hsiao, K. et al. Linkage of a prion protein missense variant to Gerstmann-Straussler syndrome. *Nature* 338, 342-345 (1989).
12. Lucas, G. J. et al. Ubiquitin-associated domain mutations of SQSTM1 in Paget's disease of bone: evidence for a founder effect in patients of British descent. *J Bone Miner. Res* 20, 227-231 (2005).
13. Newbold, R. J. et al. The destabilization of human GCAP1 by a proline to leucine mutation might cause cone-rod dystrophy. *Hum. Mol Genet* 10, 47-54 (2001).
14. Kitchens, M. E., Forsthoefel, A. M., Barbour, K. W., Spencer, H. T. & Berger, F. G. Mechanisms of acquired resistance to thymidylate synthase inhibitors: the role of enzyme stability. *Mol Pharmacol* 56, 1063-1070 (1999).
15. Murray, A. et al. Splicing mutations in KCNQ1: a mutation hot spot at codon 344 that produces in frame transcripts. *Circulation* 100, 1077-1084 (1999).
16. Wiener, R. et al. The KCNQ1 (Kv7.1) COOH terminus, a multitiered scaffold for subunit assembly and protein interaction. *J Biol Chem* 283, 5815-5830 (2008).
17. Bers, D. M. Cardiac excitation-contraction coupling. *Nature* 415, 198-205 (2002).
18. Roger, V. L. et al. Trends in heart failure incidence and survival in a community-based population. *JAMA* 292, 344-350 (2004).
19. Mahon, N. G. et al. Echocardiographic evaluation in asymptomatic relatives of patients with dilated cardiomyopathy reveals preclinical disease. *Ann. Intern. Med.* 143, 108-115 (2005).
20. Liew, C. C. & Dzau, V. J. Molecular genetics and genomics of heart failure. *Nat Rev Genet* 5, 811-825 (2004).
21. Wang, G. S. & Cooper, T. A. Splicing in disease: disruption of the splicing code and the decoding machinery. *Nat Rev Genet* 8, 749-761 (2007).
22. Matlin, A. J., Clark, F. & Smith, C. W. Understanding alternative splicing: towards a cellular code. *Nat. Rev Mol Cell Biol* 6, 386-398 (2005).
23. Benjamini, Y. & Hochberg, Y. Controlling the false discovery rate: a practical and powerful approach to multiple testing. *J Roy Statist Soc SerB* 57, 289-300 (1995).
24. Greaser, M. L. et al. Developmental changes in rat cardiac titin/connectin: transitions in normal animals and in mutants with a delayed pattern of isoform transition. *J Muscle Res Cell Motil* 26, 325-332 (2005).
25. Saar, K. et al. SNP and haplotype mapping for genetic analysis in the rat. Nat Genet 40, 560-566 (2008).
26. Hardenbol, P. et al. Multiplexed genotyping with sequence-tagged molecular inversion probes. *Nat Biotechnol* 21, 673-678 (2003).
27. Hardenbol, P. et al. Highly multiplexed molecular inversion probe genotyping: over 10,000 targeted SNPs genotyped in a single tube assay. *Genome Res* 15, 269-275 (2005).
28. Warren, C. M., Krzesinski, P. R. & Greaser, M. L. Vertical agarose gel electrophoresis and electroblotting of high-molecular-weight proteins. *Electrophoresis* 24, 1695-1702 (2003).
29. Claycomb, W. C. et al. HL-1 cells: a cardiac muscle cell line that contracts and retains phenotypic characteristics of the adult cardiomyocyte. *Proc Natl Acad Sci USA* 95, 2979-2984 (1998).
30. Gotthardt, M. et al. Conditional Expression of Mutant M-line Titins Results in Cardiomyopathy with Altered Sarcomere Structure. *J Biol Chem* 278, 6059-6065 (2003).
31. Kwan, T. et al. Genome-wide analysis of transcript isoform variation in humans. *Nat Genet* 40, 225-231 (2008).
32. Naef, F. & Magnasco, M. O. Solving the riddle of the bright mismatches: labeling and effective binding in oligonucleotide arrays. *Phys. Rev E. Stat. Nonlin. Soft. Matter Phys.* 68, 011906 (2003).

33. Saar, K. et al. SNP and haplotype mapping for genetic analysis in the rat. *Nat Genet* 40, 560-566 (2008).

34. Benjamini, Y. & Hochberg, Y. Controlling the false discovery rate: a practical and powerful approach to multiple testing. *J Roy Statist Soc Ser B* 57, 289-300 (1995).

35. Weinert, S., Bergmann, N., Luo, X., Erdmann, B., & Gotthardt, M. M line-deficient titin causes cardiac lethality through impaired maturation of the sarcomere. *J Cell Biol* 173, 559-570 (2006).

36. Ellinor, P. T. et al. A novel locus for dilated cardiomyopathy, diffuse myocardial fibrosis, and sudden death on chromosome 10q25-26. *J Am Coll Cardiol* 48, 106-111 (2006).

The invention claimed is:

1. A method for diagnosing or monitoring a cardiac disease in a biological sample obtained from a subject, comprising:
    determining the presence of a P638L mutation or a P641L mutation in a RBM20 transcript or in a RBM20 protein in a sample from a human or a rat, respectively, and
    deducing from the presence of at least a P638L mutation according to SEQ ID NO. 5 or at least a P641L mutation according to SEQ ID NO. 6 that the subject suffers from a cardiac disease.

2. The method of claim 1, wherein the cardiac disease is selected from the group consisting of cardiomyopathy and Sudden Cardiac Death (SCD).

3. The method of claim 2, wherein the cardiomyopathy is selected from the group consisting of restrictive cardiomyopathy (RCM), dilated cardiomyopathy (DCM), hypertrophic cardiomyopathy (HCM), arrhythmogenic right ventricular cardiomyopathy (ARVC).

4. A kit for diagnosing, prognosing, or monitoring a cardiac disease in a subject, comprising
    a means for determining a mutation in a RBM20 transcript or in a RBM20 protein in a biological sample from a human wherein the mutation comprises at least a P638L mutation according to SEQ ID No. 5 or at least a P641L mutation according to SEQ ID NO. 6.

5. The kit of claim 4, wherein the means for determining the P638L or the P641L mutation is selected from the group consisting of a probe for detecting the mutation, and a primer for amplifying a nucleic acid molecule encoding at least one of the mutations in an amplification reaction and/or in a sequencing reaction.

6. The method of claim 2, wherein the cardiomyopathy is a fibrotic heart disease.

7. The method of claim 2, wherein the Sudden Cardiac Death (SCD) is selected from the group consisting of arrhythmia-related death and ventricular conduction-related death.

8. The method of claim 3, wherein the cardiomyopathy is dilated cardiomyopathy (DCM).

9. The kit of claim 4, wherein the mutation is futher selected from the group consisting of R634Q, R636S, R636H and S637G.

* * * * *

SEQUENCE LISTING

```
<160> NUMBER OF SEQ ID NOS: 11

<210> SEQ ID NO 1
<211> LENGTH: 422
<212> TYPE: RNA
<213> ORGANISM: Homo sapiens

<400> SEQUENCE: 1 cucuuugcc ugccaucaug uuggauguga uucugcuccu ccuuugccuu ccacuaugau      60
ucugaggccu ccucagccau gcugaacugu uuaccuguuc uggauguuuc auauagaugg    120
agucguauga cauuuugcua cuggcuucau ugacuuaaca caguguuuuc aagguucauc    180
cacaguguag cagcuaaaag gggaagaaga ggaucagccc aaggaggagg aagaggaaaa    240
caagacaaac agccagugca gaggagagga acgugugucc agugucccga ucccugcgga    300
gcuaguagcu gagagcucug ugcccugggc accuugcagc ccugcaccug ccugccacuu    360
ccccaccgag gccaugggcc caggaguucu gcugcuccug cugguggcca cagcuuggca    420
ug                                                                   422

<210> SEQ ID NO 2
<211> LENGTH: 422
<212> TYPE: RNA
<213> ORGANISM: Homo sapiens

<400> SEQUENCE: 2
caugccaagc uguggccacc agcaggagca gcagaacucc ugggcccaug gccucggugg     60
ggaaguggca ggcaggugca gggcugcaag gugcccaggg cacagagcuc ucagcuacua    120
gcuccgcagg gaucgggaca cuggacacac guucucucuc ucugcacugg cuguuugucu    180 uguuuccuc uuccuccucc uugggcugau ccucuucuuc cccuuuuagc ugcuacacug     240
uggaugaacc uugaaaacac uguguuaagu caaugaagcc aguagcaaaa ugucaucga    300 cuccaucuau augaaacauc cagaacaggu aaacaguuca gcauggcuga ggaggccuca    360
gaaucauagu ggaaggcaaa ggaggagcag aaucacaucc aacaugaugg caggcaaaag    420
ag                                                                   422

<210> SEQ ID NO 3
<211> LENGTH: 422
<212> TYPE: DNA
<213> ORGANISM: Homo sapiens

<400> SEQUENCE: 3
ctcttttgcc tgccatcatg ttggatgtga ttctgctcct cctttgcctt ccactatgat     60
tctgaggcct cctcagccat gctgaactgt ttacctgttc tggatgtttc atatagatgg    120
agtcgtatga cattttgcta ctggcttcat tgacttaaca cagtgttttc aaggttcatc    180
cacagtgtag cagctaaaag gggaagaaga ggatcagccc aaggaggagg aagaggaaaa    240
caagacaaac agccagtgca gaggagagga acgtgtgtcc agtgtcccga tccctgcgga    300
```

```
gctagtagct gagagctctg tgccctgggc accttgcagc cctgcacctg cctgccactt    360
ccccaccgag ccatgggcc caggagttct gctgctcctg ctggtggcca cagcttggca    420
tg                                                                  422

<210> SEQ ID NO 4
<211> LENGTH: 844
<212> TYPE: DNA
<213> ORGANISM: Homo sapiens

<400> SEQUENCE: 4
catgccaagc tgtggccacc agcaggagca gcagaactcc tgggcccatg gcctcggtgg     60
ggaagtggca ggcaggtgca gggctgcaag gtgcccaggg cacagagctc tcagctacta   120
gctccgcagg gatcgggaca ctggacacac gttcctctcc tctgcactgg ctgtttgtct   180
tgttttcctc ttcctcctcc ttgggctgat cctcttcttc ccctttagc tgctacactg    240 tggatgaacc ttgaaaacac tgtgttaagt caatgaagcc agtagcaaaa tgtcatacga   300
ctccatctat atgaaacatc cagaacaggt aaacagttca gcatggctga ggaggcctca   360
gaatcatagt ggaaggcaaa ggaggagcag aatcacatcc aacatgatgg caggcaaaag   420
agcatgccaa gctgtggcca ccagcaggag cagcagaact cctgggccca tggcctcggt   480
ggggaagtgg caggcaggtg cagggctgca aggtgcccag gcacagagc tctcagctac    540 tagctccgca gggatcggga cactggacac acgttcctct cctctgcact ggctgtttgt   600
cttgttttcc tcttcctcct cttgggctg atcctcttct tccccttta gctgctacac     660 tgtggatgaa ccttgaaaac actgtgttaa gtcaatgaag ccagtagcaa aatgtcatac   720
gactccatct atatgaaaca tccagaacag gtaaacagtt cagcatggct gaggaggcct   780
cagaatcata gtggaaggca aaggaggagc agaatcacat ccaacatgat ggcaggcaaa   840
agag                                                                844

<210> SEQ ID NO 5
<211> LENGTH: 753
<212> TYPE: DNA
<213> ORGANISM: Homo sapiens

<400> SEQUENCE: 5
ccatgattgt gaggcctccc tacccacgtg gaactttaca agcggtaata caaagagaca     60
ggattatatg atctccaagg tcccatccag cccatttaac acggcattgt ggctctggag   120
acctggaagc actgctaact gttctctcga ttttctgacg ctcggccaca tcaacctgtc   180
atactagttg tgaggagaag tcaaggacag tgacacagcc agccagtctg aggcattttc   240
catcatcctg aaggagttgc cctatcctgc ttttcactgg aggggcatg atgggggct    300 cctgacacac tgacctctgt cagttccttc agcacaccag gctaatcccc agtcttgcgc   360
ctttggacca gaggttttct ttgctcagaa tactgtttca acagatcttt gcatagctgg   420
ctctcgctat ttgactaaaa tgtcaatcct cagagaggta ctccttaaat atccaatctt   480
aagtagcatc cctttctccc aggatcctgt ttttcagaac tctgtttctc ttttaaaaca   540
cttgttatct gaaaggatgt tgtctgcttg cttgtttgtt catttcttta ttgtctattc   600
catctcaccc cttctcagga tgtaagctgt ttaaaggcaa ggaccttatc tgtgttacat   660
gctgtattcc cagggctcag acagagcatg acctatcgta tgtactaaat aaatatctcc   720
tcatactgta aaaaaaaaaa aaaaaaaaa aaa                                 753
```

```
<210> SEQ ID NO 6
<211> LENGTH: 823
<212> TYPE: DNA
<213> ORGANISM: Homo sapiens

<400> SEQUENCE: 6
ccatgattgt gaggcctccc cagccatatg gaaatataat gcagcaacaa gctgccatct      60
tgaaagtgga gaccaggacc ttcacaagac attgaacccg acagcacctt gatcttcaac     120
ttcccaagtt ccaagaaaag ttccttcaac ctctgatcac tcaaataatc cttgttcatc     180
tctgaagacc aatttcaact tcaggcctg actgcaccat ctccagctct ctgcttcggg      240
ttgctgacct ctatgtccat accagccagg gtccctttcc ctttgactcc tggttggtaa     300
ggcaatgatg gagtattagg agacagaaga tgaatgaggt caaggcattt atttccatag     360
ttcttttctg tggggttgct aaggttggct ctctcaacca caactataat ttcacaggga     420
gtaccttatg accagttaat aaaggaagaa aaattgcaag cttagattaa ataagaattc     480
accgatatgc tagcaactgc tagcagttgc ttctttataa ccctactgat gcatggtcct     540
gcaagtcagt gagtgaaagg aaatcgttcc atcaggcaga aatttagagg ggaaatttga     600
ctgagcactg tgtgaaggga gagatggctt gaggtaggaa cctgaactaa accatgagca     660
gtagctaaca ggttcgccag ctggtaaggg aactgcaaag aacatgattg gaaagttgat     720
gatcaggaga tctcatggag gagtacatta acagtcctct cgcaacaggc cccatgttca     780
ttaatcaatt aaaaatgttt gagtaaaaaa aaaaaaaaaa aaa                       823

<210> SEQ ID NO 7
<211> LENGTH: 814
<212> TYPE: DNA
<213> ORGANISM: Homo sapiens

<400> SEQUENCE: 7
gatttgaggc ctcctcagcc atgcagaact gtcatttcaa agccttagaa actggcctca      60
acagtaactg caggaagcat acttgtcaga tctgagcaat aaaaatacac cctgactgct     120
gagcctggag cacgggagag cctacagcta accaggaag acatgcttta gataaagtcc      180
ttccaacatc ttgcaacctg gataacagcc aagtcctatt catccctctc aacctggctc     240
ttccatgccc tcctgcaagg ccttccccag cccttctctg tggatgcccc tcctccgttt     300
tgaagcagac tggataccag ccccaccccg ccgccatgct tctttttatcc ttgcagcttc    360 actcctgagg ctggcgagac cacaaaccca ccaggagaaa tgaactccag acgggaagaa     420
tgaacaactc ctgatgcacc accttaagag ctgtaacacg caccgccaag gtttgcagat     480
tcactcctga agccagcgag accacgaacc caccagaagg aagaaactct gaacacgtcc     540
gaacatcaga aggaacaaac tctggatacg ccatctttaa gaactgtaac actcaccacg     600
agggtccacg acttcattct tgaagtcagt gagaccaaga acccaccaat tctggacaca     660
atttcatttg gtgagcagtc cagattacat gtgtgtacac tgtaatgatc agctaaggac     720
tgactgcctt tagctccttc acccgttctc acctctgagg ttcagtaata aatggctcct     780
accaactaac tgaagtatca aaaaaaaaaa aaaa                                 814

<210> SEQ ID NO 8
<211> LENGTH: 414
<212> TYPE: DNA
<213> ORGANISM: Homo sapiens

<400> SEQUENCE: 8
```

```
gattctgagg cctcctcagc catgtggaac ttttttttcta gcttgtgttg tgtttttaat      60
gggagagttg gtcagcgtct gctggaacag agctacgcct atggaaccgt agacttgttc     120
gtgctttatt gcaatacttt aaagacacaa agtctcaaca accatcttcc gcttgacgag     180
acagatcact ctaatttgag cagaagctac tatgtcctgc cctttgaacg cggcggcccg     240
gacagctgac aaggacacac tgtgtatttc cattccaatt ctgggagtgc tctgaggcct     300 ctggggaga aggacccatg aaatattcaa acataagtg aataaatat ctaggtgcta     360 gatatgggcc aggaagagcc ctcggccctg caaaaaaaaa aaaaaaaaaa aaaa           414

<210> SEQ ID NO 9
<211> LENGTH: 422
<212> TYPE: DNA
<213> ORGANISM: Homo sapiens

<400> SEQUENCE: 9
gagaaaacgg acggtagtac aacctacact aagacgagga ggaaacggaa ggtgatacta      60
agactccgga ggagtcggta cgacttgaca aatggacaag acctacaaag tatatctacc     120
tcagcatact gtaaaacgat gaccgaagta actgaattgt gtcacaaaag ttccaagtag     180
gtgtcacatc gtcgattttc cccttcttct cctagtcggg ttcctcctcc ttctccttt     240 gttctgtttg tcggtcacgt ctcctctcct tgcacacagg tcacagggct agggacgcct     300
cgatcatcga ctctcgagac acgggacccg tggaacgtcg ggacgtggac ggacggtgaa     360
ggggtggctc cggtacccgg gtcctcaaga cgacgaggac gaccaccggt gtcgaaccgt     420
ac                                                                    422

<210> SEQ ID NO 10
<211> LENGTH: 422
<212> TYPE: DNA
<213> ORGANISM: Homo sapiens

<400> SEQUENCE: 10
gtacggttcg acaccggtgg tcgtcctcgt cgtcttgagg acccgggtac cggagccacc      60
ccttcaccgt ccgtccacgt cccgacgttc cacgggtccc gtgtctcgag agtcgatgat     120
cgaggcgtcc ctagccctgt gacctgtgtg caaggagagg agacgtgacc gacaaacaga     180
acaaaaggag aaggaggagg aacccgacta ggagaagaag gggaaaatcg acgatgtgac     240
acctacttgg aacttttgtg acacaattca gttacttcgg tcatcgtttt acagtatgct     300
gaggtagata tactttgtag gtcttgtcca tttgtcaagt cgtaccgact cctccggagt     360
cttagtatca ccttccgttt cctcctcgtc ttagtgtagg ttgtactacc gtccgttttc     420
tc                                                                    422

<210> SEQ ID NO 11
<211> LENGTH: 181
<212> TYPE: DNA
<213> ORGANISM: Homo sapiens

<400> SEQUENCE: 11
aagacaaaca gccagtgcag aggagaggaa cgtgtgtcca gtgtcccgat ccctgcggag      60
ctagtagctg agagctctgt gccctgggca ccttgcagcc ctgcacctgc ctgccacttc     120
cccaccgagg ccatgggccc aggagttctg ctgctcctgc tggtggccac agcttggcat     180
g                                                                     181
```